United States Patent
Ogo

(10) Patent No.: US 10,287,556 B2
(45) Date of Patent: May 14, 2019

(54) LUCIFERASE SHOWING ORANGE LUMINESCENCE

(71) Applicant: OLYMPUS CORPORATION, Tokyo (JP)

(72) Inventor: Katsunori Ogo, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/472,919

(22) Filed: Mar. 29, 2017

(65) Prior Publication Data
US 2017/0204379 A1      Jul. 20, 2017

Related U.S. Application Data

(63) Continuation of application No. PCT/JP2014/076113, filed on Sep. 30, 2014.

(51) Int. Cl.
    *C12N 9/02* (2006.01)
(52) U.S. Cl.
    CPC .... *C12N 9/0069* (2013.01); *C12Y 113/12007* (2013.01)
(58) Field of Classification Search
    CPC .................................................. C12N 9/0069
    See application file for complete search history.

(56) References Cited

U.S. PATENT DOCUMENTS

| | | | |
|---|---|---|---|
| 5,219,737 A | 6/1993 | Kajiyama et al. | |
| 2003/0166905 A1 | 9/2003 | Wood et al. | |
| 2009/0305353 A1 | 12/2009 | Fujii et al. | |

FOREIGN PATENT DOCUMENTS

| | | | |
|---|---|---|---|
| JP | H03-285683 A | 12/1991 | |
| JP | H08-510387 A | 11/1996 | |
| JP | 2007-097577 A | 4/2007 | |
| JP | 2007-218774 A | 8/2007 | |
| JP | 2008-289475 A | 12/2008 | |
| JP | 2011-188787 A | 9/2011 | |
| JP | 2012-235756 A | 12/2012 | |
| JP | 2013-081459 A | 5/2013 | |
| JP | 2013-118831 A | 6/2013 | |
| JP | 2014-018191 A | 2/2014 | |
| JP | 2014-060941 A | 4/2014 | |

OTHER PUBLICATIONS

PIR database Acc# S33788 from Devine et al, Luciferase from the East European firefly Luciola mingrelica: cloning and nucleotide sequence of the cDNA, overexpression in *Escherichia coli* and purification of the enzyme. Biochim. Biophys. Acta 1173, 121-132, 1993. Alignment with SEQ ID No: 42.*
International Search Report dated Jan. 6, 2015 issued in PCT/JP2014/076113.
Japanese Office Action dated Feb. 28, 2017 issued in JP 2013-148455, with English translation SLS Aug. 21, 2018.
Wang, Yu et al., "Impact of Site-Directed Mutant Luciferase on Quantitative Green and Orange/Red Emission Intensities in Firefly Bioluminescence", Scientific Reports (Aug. 23, 2013), vol. 3, 2490, pp. 1-6.
Naylor L. H., "Reporter Gene Technology: The Future Looks Bright", Biochemical Pharmacology (1999), vol. 58, vol. 5, pp. 749-757, cited in spec on p. 4.
Nakajima, Yoshihiro et al., Multicolor luciferase assay system: one-step monitoring of multiple gene expressions with a single substrate, BioTechniques (2005), vol. 38, No. 6, pp. 891-894, cited in spec on p. 4.
Viviani, V.R. et al., "Cloning and Molecular Characterization of the cDNA for the Brazilian Larval Click-beetle Pyrearinus termitilluminans Luciferase", Photochemistry and Photobiology (1999), vol. 70, No. 2, pp. 254-260, cited in spec on p. 4.
English translation of International Preliminary Report on Patentability dated Apr. 13, 2017 together with the Written Opinion received in related International Application No. PCT/JP2014/076113.

* cited by examiner

*Primary Examiner* — Sheridan Swope
(74) *Attorney, Agent, or Firm* — Scully, Scott, Murphy & Presser, P.C.

(57) ABSTRACT

A luciferase that includes an amino acid sequence in which a mutation is introduced into an amino acid sequence of a luciferase derived from *Luciora kuroiwae*. The luciferase catalyzes a luminescence reaction that generates luminescence having the maximum luminescent wavelength of 570 nm to 610 nm. The luminescence has an intensity at least 10 times higher than that of luminescence generated in a luminescence reaction catalyzed by a luciferase derived from *Rhagophthalmus ohbai*.

16 Claims, 2 Drawing Sheets

Specification includes a Sequence Listing.

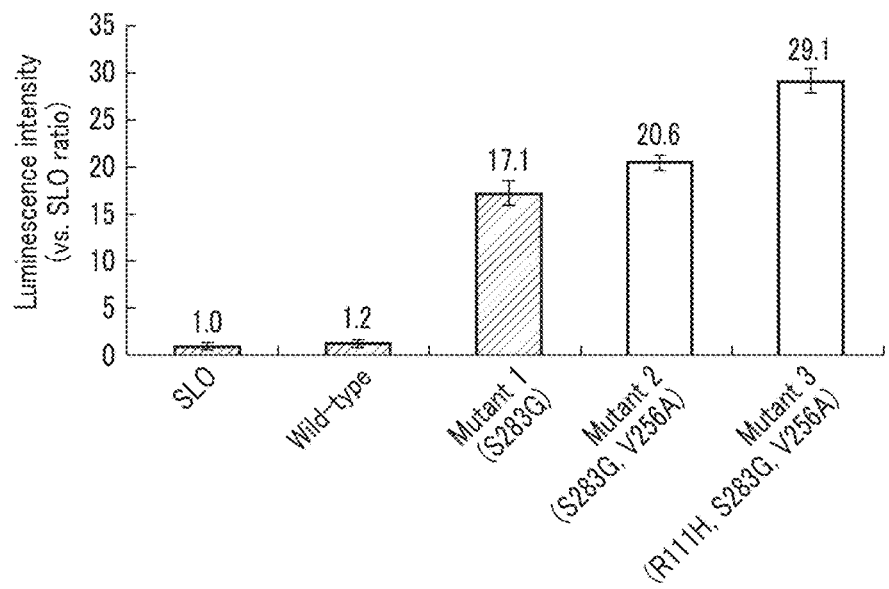
F I G. 2
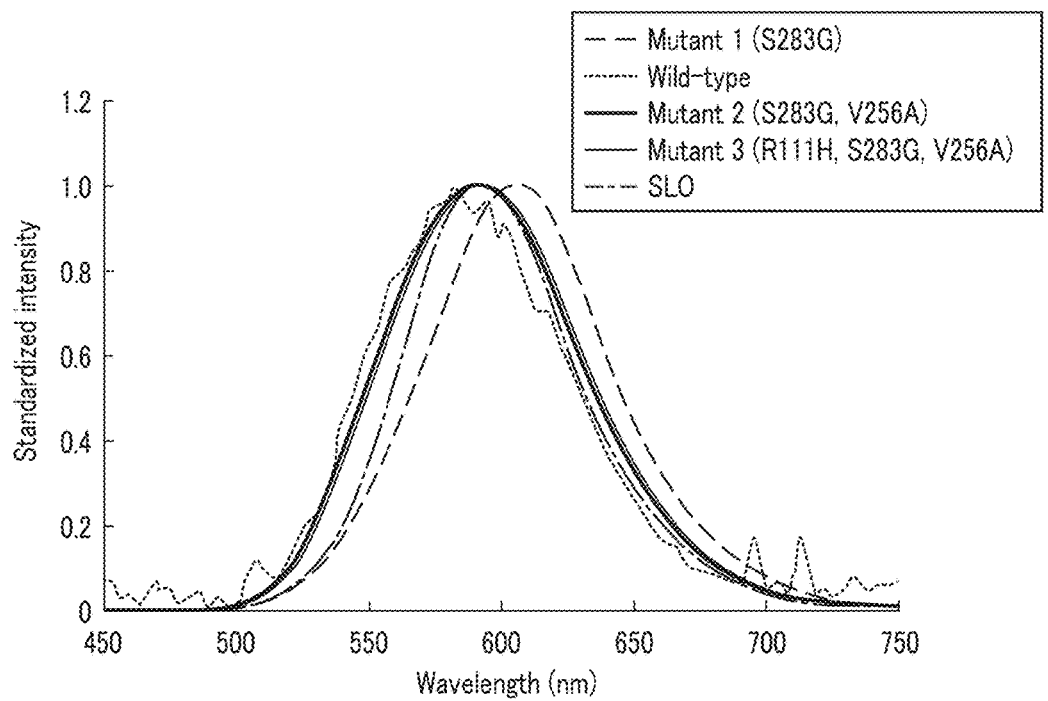
F I G. 3

LUCIFERASE SHOWING ORANGE LUMINESCENCE

CROSS-REFERENCE TO RELATED APPLICATIONS

This application is a Continuation Application of PCT Application No. PCT/JP2014/076113, filed Sep. 30, 2014, the entire contents of which are incorporated herein by reference.

INCORPORATION BY REFERENCE OF SEQUENCE LISTING

The Sequence Listing in an ASCII text file, named as 34822Z_Sequence_Listing.txt of 54 KB, created on Mar. 27, 2017, and submitted to the United States Patent and Trademark Office via EFS-Web, is incorporated herein by reference.

BACKGROUND OF THE INVENTION

1. Field of the Invention

The present invention relates to a luciferase showing orange luminescence.

2. Description of the Related Art

In order to examine cell functions such as intracellular signal transduction and gene expression, fluorescent probes such as fluorochrome and fluorescent protein, and chemiluminescent probes utilizing a luciferin-luciferase reaction are used.

In particular, in an analysis of gene expression regulation, a luminescent measurement is used which does not cause damages to cells by exciting light, does not have a problem of self-luminescence, and excellent in quantitativity. For example, when cells to which a luciferase gene is transferred are observed, an expression intensity (specifically, an expression amount) of the luciferase gene can be examined by measuring an intensity of luminescence derived from the luciferase activity of the cells. Specifically, first, the cells are lysed to prepare a cell lysate; then luciferin, adenosine triphosphate (ATP), and the like are added to the resulting cell lysate; a luminescence intensity is quantified with a luminometer using a photomultiplier; and an expression amount is determined based on the quantified results.

According to the method, the luminescence intensity is measured after the cells are lysed. For that reason, an expression amount of the luciferase gene at a certain point of time is obtained as an average value of all cells used in the measurement.

As a method of transferring a luminescent gene such as a luciferase gene as a reporter gene, for example, a calcium phosphate method, a lipofection method, or an electroporation method can be used, and these methods are properly used depending on the purpose and the type of cell. A target DNA fragment is linked to the upstream or downstream of a luciferase gene intended to be transferred to a cell, and an expression amount of the luciferase gene is measured, whereby the influence of the DNA fragment on the transcription of the luciferase gene can be examined. In addition, when the target gene is co-expressed with the luciferase gene transferred to the cell, the influence of the gene product on the expression of the luciferase gene can be examined.

In order to analyze an expression amount of the luminescent gene with the passage of time, it is necessary to measure a luminescence intensity of living cells over time. Such a measurement is performed by culturing cells in an incubator equipped with a luminometer, and measuring a luminescence intensity of the whole cell population at regular time intervals. An expression rhythm with a fixed periodicity can be analyzed by observing the time-dependent change in the expression amount of the luminescent gene in the whole cell population.

It is difficult, however, to quantify transcription activity of the target gene in the case of an analysis using one type of luciferase as a reporter, because there is no internal control. Therefore, methods using plural types of luciferases showing a different luminescent color as a reporter, such as a dual assay (the following NON-PATENT LITERATURE 1) or a multicolor assay (the following PATENT LITERATURE 1 and NON-PATENT LITERATURE 2) have been established.

In particular, the multicolor assay is performed by using a sample containing plural types of luminescent enzymes showing a different color, such as a luciferase showing the maximum luminescent wavelength at about 550 nm (green luminescence), a luciferase showing the maximum luminescent wavelength at about 580 nm (orange luminescence), and a luciferase showing the maximum luminescent wavelength at about 620 nm (red luminescence), and simultaneously measuring and calculating a relative quantity of light shown by each luminescent enzyme.

When all of the luciferases used in the multicolor assay are derived from the same species of firefly, multiple luminescent colors can be simultaneously detected using a single type of a substrate. Examples of such luciferases which have been commercially available, include luciferases derived from Iriomote firefly *Rhagophthalmus ohbai*, such as a green luciferase (SLG luciferase: Toyobo Co., Ltd.), an orange luciferase (SLO luciferase: Toyobo Co., Ltd.) and a red luciferase (SLR luciferase: Toyobo Co., Ltd.) (the following PATENT LITERATURE 1).

PRIOR-ART LITERATURE

Patent Literature

PATENT LITERATURE 1: Jpn. Pat. Appln. KOKAI Publication 2007-218774

Non-Patent Literatures

NON-PATENT LITERATURE 1: Naylor L. H. (1999) Biochem. Pharmacol., 58 (5): 749-757, Reporter gene technology: the future looks bright.

NON-PATENT LITERATURE 2: Nakajima, Y., T. Kimura, K. Sugata, T. Enomoto, T. Asakawa, H. Kubota, M. Ikeda, and Y. Ohmiya., (2005) BioTechniques, 38: 891-894, A multicolor luciferase assay system, one-step monitoring of multiple gene expressions with a single substrate.

NON-PATENT LITERATURE 3: Viviani V R, Silva A C, Perez G L, Santelli R V, Bechara E J, Reinach F C., (1999) Photochem. Photobiol., 70 (2): 254-260, Cloning and molecular characterization of the cDNA for the Brazilian larval click-beetle *Pyrearinus termitilluminans* luciferase.

BRIEF SUMMARY OF THE INVENTION

It is an object of the present invention to provide a luciferase showing orange luminescence at a high brightness.

A luciferase according to an embodiment comprises an amino acid sequence in which a mutation is introduced into an amino acid sequence of SEQ ID NO: 38. The luciferase catalyzes a luminescence reaction that generates luminescence having the maximum luminescent wavelength of 570 nm to 610 nm. The luminescence has an intensity at least 10 times higher than that of luminescence generated in a luminescence reaction catalyzed by a luciferase having an amino acid sequence of SEQ ID NO: 48.

According to the present invention, there is provided a luciferase showing orange luminescence at a high brightness.

BRIEF DESCRIPTION OF THE SEVERAL VIEWS OF THE DRAWING

FIG. 2 is a view showing luminescence intensities of luminescence excited by various types of luciferases in a case where D-luciferin is used as a substrate.

FIG. 3 is a view showing luminescence spectrums of luminescence excited by various types of luciferases in a case where D-luciferin is used as a substrate.

DETAILED DESCRIPTION OF THE INVENTION

Figure 1:
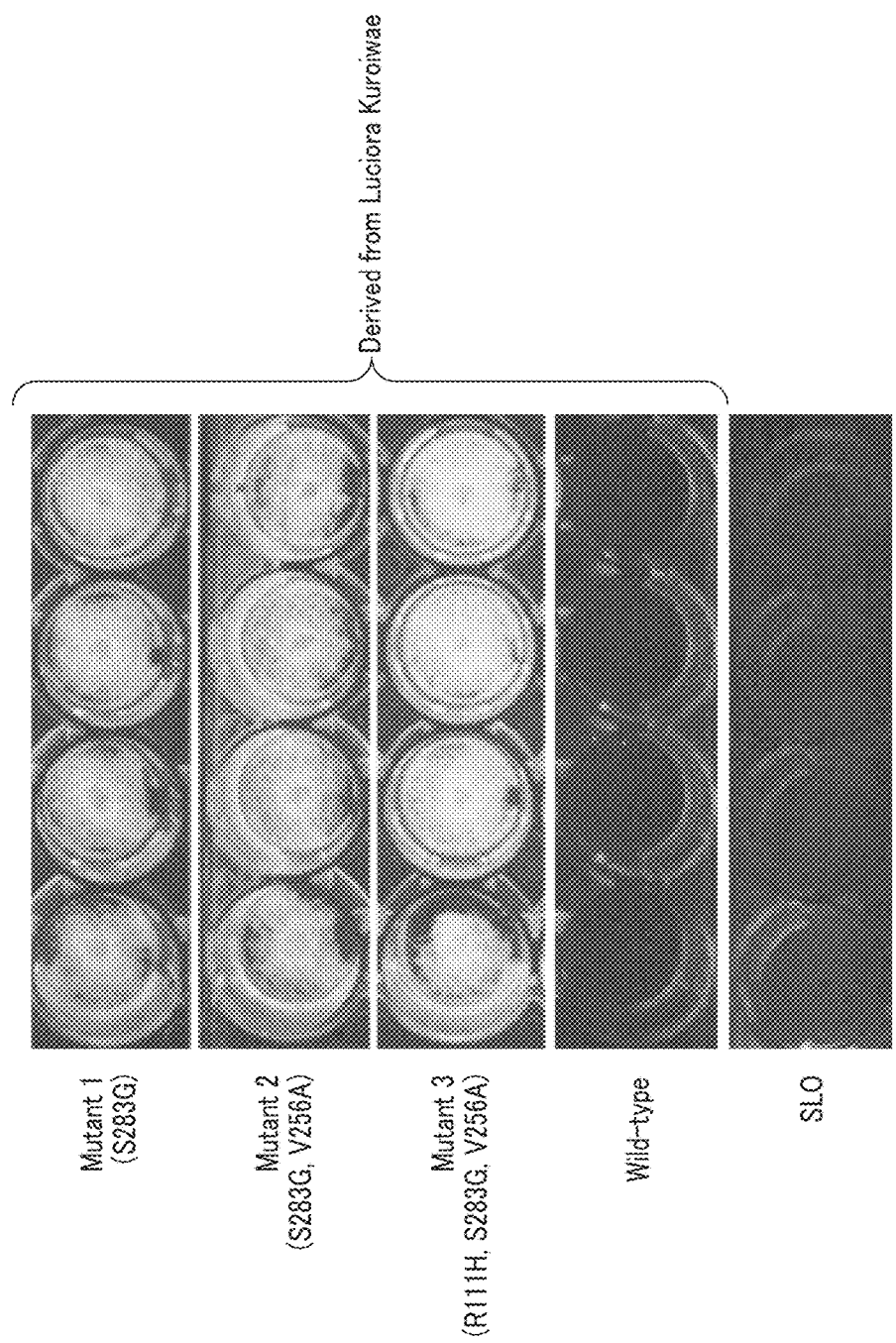
FIG. 1 is a view showing luminescence excited in HeLa cells containing various types of luciferases in a case where D-luciferin is used as a luminescent substrate.

A first embodiment of the present invention is a luciferase.

The "luciferase" generally refers to an enzyme which catalyzes a chemical reaction causing luminescence. A substance which serves as a substrate of the enzyme is called "luciferin." When the luciferin is chemically changed by catalysis of the luciferase in the presence of ATP, luminescence occurs. At this time, luciferases derived from firefly and luciferases derived from a bacterium are obtained. The luciferase according to the embodiment has the same definition as described above, and the luciferase is derived from firefly described below.

With respect to the embodiment, the luciferin means a luciferin and an analog thereof which serve as a substrate of firefly luciferase. The luciferin is, for example, substances described as a substrate in WO 2009/096197 and WO 2010/106896. Specifically, they include, for example, dimethylaniline-monoene type luciferins, dimethylaniline-diene type luciferins, dimethylaniline type luciferins, D-luciferin, and derivatives thereof.

The luciferase according to the embodiment has an amino acid sequence in which a mutation is introduced into an amino acid sequence of SEQ ID NO: 38

The amino acid sequence of SEQ ID NO: 38 is a sequence in which a mutation is introduced into the amino acid sequence (SEQ ID NO: 1) of a wild type luciferase obtained from *Luciora kuroiwae*. *Luciora kuroiwae* is a firefly belonging to the genus *Luciola*, the family Lampyridae, the order Coleoptera, the class Insecta, the phylum Arthropoda. The amino acid sequence of SEQ ID NO: 38 is a sequence in which a serine residue at the 283rd position from the N-terminal side in the amino acid sequence of SEQ ID NO: 1 is substituted by a glycine residue. In the present application, the substitution mutation as described above may be expressed as "S283G mutation" or "S283G", and the luciferase having the amino acid sequence of SEQ ID NO: 38 may be expressed as "S283G mutant" or "mutant 1."

The wild type luciferase obtained from *Luciora kuroiwae* has the following amino acid sequence:

(SEQ ID NO: 1)
MEKEENVIYGPEPFYPVEEGSAGTQLHRFMERYAKMGAICFSNALTGQDV
TYAEYFDRSVRLAEALRRHGLTPEKKIGICSENCLEFFIPVLSGAYIASP
VAPTNEIYTIRELVHSFGISEPMIVFSSKKGLDKVLEVQKTVHSIKTIVI
IDSSTTYRGYDSMDAFVKKYVPANFNLSEFKTVEVDNETHTLLIMNSSGS
TGLPKGVLVRHCGAVTRFSHCRDPIFGNQVSPGTAILTVVPFHHGFGMFT
TLGYFVCGYRIVMLTKFDDEVLLKTLQDYKCTSVILVPTLFAILNRSELL
EKFDLSNLTEIASGGAPLAKEVGEAVARRFNLPGVRQGYGLTETTSAFII
TPEGDDKPGASGKVVPLMKVKVIDLDTKKTLGPNRRGEICVKGPMLMTGY
EKNPTETKEIIDEDGWLHSGDIGYWDEDHHFFIVDRLKSLIKYKGYQVPP
AELESVLLQHPNIFDAGVAGIPDPEAGELPGAVVVLEKGKHLTEQEVLDY
VAGQVYNAKRLRGGVRFVDEVPKGLTGKIDAKAIREILKKPQAKM

The S283G mutant (mutant 1) has the following amino acid sequence:

(SEQ ID NO: 38)
MEKEENVIYGPEPFYPVEEGSAGTQLHRFMERYAKMGAICFSNALTGQDV
TYAEYFDRSVRLAEALRRHGLTPEKKIGICSENCLEFFIPVLSGAYIASP
VAPTNEIYTIRELVHSFGISEPMIVFSSKKGLDKVLEVQKTVHSIKTIVI
IDSSTTYRGYDSMDAFVKKYVPANFNLSEFKTVEVDNETHTLLIMNSSGS
TGLPKGVLVRHCGAVTRFSHCRDPIFGNQVSPGTAILTVVPFHHGFGMFT
TLGYFVCGYRIVMLTKFDDEVLLKTLQDYKCTGVILVPTLFAILNRSELL
EKFDLSNLTEIASGGAPLAKEVGEAVARRFNLPGVRQGYGLTETTSAFII
TPEGDDKPGASGKVVPLMKVKVIDLDTKKTLGPNRRGEICVKGPMLMTGY
EKNPTETKEIIDEDGWLHSGDIGYWDEDHHFFIVDRLKSLIKYKGYQVPP
AELESVLLQHPNIFDAGVAGIPDPEAGELPGAVVVLEKGKHLTEQEVLDY
VAGQVYNAKRLRGGVRFVDEVPKGLTGKIDAKAIREILKKPQAKM

The mutation which is introduced into the amino acid sequence of SEQ ID NO: 38 is, for example, substitution, deletion and/or addition of the amino acid residue. The mutation may be introduced into one site on the amino acid sequence of SEQ ID NO: 38, or may be introduced into multiple sites on the amino acid sequence of SEQ ID NO: 38. The amino acid sequence of the luciferase according to the embodiment and the original amino acid sequence of SEQ ID NO: 38 may have a given homology. For example, the amino acid sequences have a homology of 80% or more, 85% or more, 90% or more, 95% or more, 96% or more, 97% or more, 98% or more, 99% or more, 99.5% or more, or 99.8% or more.

The luciferase according to the embodiment catalyzes a luminescence reaction which generates luminescence having the maximum luminescent wavelength of 570 nm to 610 nm.

The light having a wavelength of 570 nm to 610 nm is generally orange light. The maximum luminescent wavelength of the luminescence caused by the luciferase according to the embodiment is preferably within a range of 580 nm to 600 nm, more preferably 585 nm to 595 nm, most preferably about 590 nm.

The luminescence caused by the luciferase according to the embodiment has the maximum luminescent wavelength in the range described above, but lights having wavelengths beyond the range may be contained. It is preferable, however, that the light intensity of the wavelengths beyond the range is small.

According to the luciferase of the embodiment, the orange luminescence can be obtained at a temperature suitable for culture of organisms. Preferably, according to the luciferase of the embodiment, the orange luminescence can be obtained in a temperature range suitable for culture of mammal cells, where the temperature is, for example, from 32° C. to 42° C., more specifically from 35° C. to 39° C., particularly about 37° C.

According to the luciferase of the embodiment, the luminescence having an intensity higher than that of the conventional orange luciferase can be obtained. For example, the luminescence has an intensity at least 10 times higher, preferably at least 20 times higher, more preferably at least 29 times higher, than that of an orange luciferase derived from *Rhagophthalmus ohbai* (which is commercially available as SLO luciferase from Toyobo Co., Ltd.).

The SLO luciferase (manufactured by Toyobo Co., Ltd.) has the following amino acid sequence:

(SEQ ID NO: 48)
MANEIILHGAKPRDPLDLGTAGIQLYRALTNFSFLREALIDAHTEEVVSY

ADILENSCRLAKCYENYGLRQNSVISVCSENSTIFFYPVIAALYMGVITA

TVNDSYTERELLETLNISKPELVFCSKKAIKNMMALKRNVNFIKKVVLLD

SKEDMGEAQCLSNFMARYSEPNLDVRNFKPRDFDAKEQVALIMSSSGTTG

LPKGVVLTHRNLSVRFVHCKDPLFGNRTIPSTSILSIVPFHHAFGMFTTL

SYFIVGLRVVLLKRFEEKFFLSTIEKYRIPTIVLAPPVMVFLAKSPLVDQ

YDLSSIREVATGGAPVGTEVAVAVAKRLKIGGILQGYGLTETCCAVLITP

HDDVKTGSTGRVAPYVQAKIVDLTTGKSLGPNKRGELCFKSEIIMKGYFN

NKQATEEAIDKEGWLHSGDVGYYDDDGHFFVVDRLKELIKYKGYQVAPAE

LEWLLLQHPSIKDAGVTGVPDEAAGELPGACIVLQEGKSLTEQEIIDYIA

ERVSPTKRIRGGVVFVDDIPKGATGKLVRSELRKLLAQKKSKL

In addition, the gene of the SLO luciferase (manufactured by Toyobo Co., Ltd.) has the following base sequence:

(SEQ ID NO: 49)
ATGGCTAACGAGATCATCCTGCACGGCGCCAAGCCCAGGGACCCCCTGGA

CCTGGGCACCGCCGGCATTCAGCTCTACAGGGCCCTGACCAACTTCTCCT

TCCTGAGGGAGGCCCTGATCGACGCCCACACCGAGGAGGTGGTGTCTTAC

GCCGACATCCTGGAGAACAGCTGTAGACTGGCTAAGTGCTACGAGAACTA

CGGCCTGCGCCAGAACAGCGTGATCTCCGTGTGCAGCGAGAATAGCACCA

TCTTCTTCTACCCCGTGATCGCCGCCCTGTACATGGGCGTGATCACCGCC

ACCGTGAACGACAGCTACACCGAGCGGGAGCTGCTGGAGACCCTGAACAT

CTCCAAGCCCGAACTGGTGTTCTGCTCCAAGAAGGCCATCAAGAACATGA

TGGCCCTGAAGAGGAACGTGAACTTCATCAAGAAGGTGGTGCTGCTGGAC

AGCAAGGAGGATATGGGCGAGGCCCAGTGCCTGAGCAACTTCATGGCCCG

GTACTCCGAGCCCAACCTGGACGTGAGAAACTTCAAGCCAAGGGACTTCG

ACGCCAAGGAGCAGGTGGCCCTTATTATGTCCTCCTCTGGCACCACCGGC

CTGCCAAAGGGCGTGGTGCTGACCCACAGGAACCTGAGCGTGCGCTTCGT

CCACTGCAAGGACCCCCTGTTCGGCAACAGAACCATCCCCTCCACCTCA

TCCTGTCCATCGTGCCCTTCCACCACGCCTTCGGAATGTTCACAACCCTG

TCCTACTTCATCGTGGGCCTGAGAGTGGTGCTGCTGAAGAGATTCGAGGA

GAAGTTCTTCCTGAGCACCATCGAGAAGTACAGAATCCCAACAATCGTGC

TGGCCCCTCCTGTGATGGTGTTCCTGGCTAAGAGCCCCCTGGTGGACCAG

TACGACCTGTCCAGCATCAGAGAGGTGGCCACCGGCGGCGCCCCTGTGGG

CACCGAGGTTGCCGTGGCCGTGGCCAAGCGGCTGAAGATCGGCGGCATCC

TCCAGGGCTACGGCCTGACCGAGACCTGCTGCGCCGTGCTGATCACCCCC

CACGACGACGTGAAGACCGGCTCCACCGGCAGGGTAGCCCCCTACGTGCA

GGCTAAGATCGTGGACCTGACCACCGGCAAGTCCCTGGGACCTAACAAGA

GAGGCGAGCTGTGCTTCAAGAGCGAGATCATCATGAAGGGCTACTTCAAC

AACAAGCAGGCCACCGAGGAGGCCATCGACAAGGAGGGCTGGCTGCACTC

CGGCGACGTGGGATACTACGACGACGATGGACATTTCTTCGTGGTGGACC

GGCTGAAAGAGCTGATCAAGTACAAGGGCTACCAGGTGGCCCCCGCCGAG

CTGGAGTGGCTGCTGCTCCAGCACCCATCCATCAAGGATGCCGGCGTGAC

CGGCGTGCCCGACGAGGCCGCCGGCGAGCTGCCCGGCGCCTGCATCGTGC

TCCAGGAGGGCAAGAGCCTGACCGAGCAGGAGATCATCGACTACATCGCC

GAGCGAGTGTCTCCCACCAAGCGCATCCGGGGCGGAGTCGTCTTCGTGGA

CGACATCCCCAAGGGCGCCACCGGCAAGCTGGTGAGAAGCGAGCTGCGGA

AGCTGCTGGCCCAGAAGAAGTCCAAGCTGTAA

One of specific examples of the luciferase according to the embodiment is a luciferase having the amino acid sequence of SEQ ID NO: 40. In this amino acid sequence, a substitution of one amino acid residue is introduced into the amino acid sequence of SEQ ID NO: 38. Specifically, a valine residue at the 256th position from the N-terminal side in the amino acid sequence of SEQ ID NO: 38 is substituted by an alanine residue. This substitution mutation may be expressed as "V256A mutation" or "V256A" in the present application. The luciferase having the amino acid sequence of SEQ ID NO: 40 has mutations of S283G and V256A, based on the amino acid sequence (SEQ ID NO: 1) of the wild type luciferase derived from *Luciora kuroiwae*. In the present application, the luciferase having the amino acid sequence of SEQ ID NO: 40 may be expressed as "mutant 2."

The mutant 2 has the following amino acid sequence:

(SEQ ID NO: 40)
MEKEENVIYGPEPFYPVEEGSAGTQLHRFMERYAKMGAICFSNALTGQDV

TYAEYFDRSVRLAEALRRHGLTPEKKIGICSENCLEFFIPVLSGAYIASP

VAPTNEIYTIRELVHSFGISEPMIVFSSKKGLDKVLEVQKTVHSIKTIVI

IDSSTTYRGYDSMDAFVKKYVPANFNLSEFKTVEVDNETHTLLIMNSSGS

TGLPKGVLVRHCGAVTRFSHCRDPIFGNQVSPGTAILTVVPFHHGFGMFT

TLGYFACGYRIVMLTKFDDEVLLKTLQDYKCTGVILVPTLFAILNRSELL

EKFDLSNLTEIASGGAPLAKEVGEAVARRFNLPGVRQGYGLTETTSAFII

TPEGDDKPGASGKVVPLMKVKVIDLDTKKTLGPNRRGEICVKGPMLMTGY

EKNPTETKEIIDEDGWLHSGDIGYWDEDHHFFIVDRLKSLIKYKGYQVPP

-continued

AELESVLLQHPNIFDAGVAGIPDPEAGELPGAVVVLEKGKHLTEQEVLDY

VAGQVYNAKRLRGGVRFVDEVPKGLTGKIDAKAIREILKKPQAKM

Another specific example of the luciferase according to the embodiment is a further mutant having additional mutation(s) in the mutant 2 but maintaining the luminescence properties of the mutant 2. Specifically, the further mutant has an amino acid sequence which has 80% or more homology to the amino acid sequence of SEQ ID NO: 40 and which has a glycine residue and an alanine residue at the 283rd and 256th positions from the N-terminal side, respectively; the further mutant catalyzes a luminescence reaction generating luminescence having the maximum luminescent wavelength of 570 nm to 610 nm; and the luminescence has an intensity at least 10 times higher than that of luminescence generated in a luminescence reaction catalyzed by a luciferase having an amino acid sequence of SEQ ID NO: 48.

The homology between the amino acid sequence of the mutant 2 and the amino acid sequence of the further mutant of the mutant 2 is preferably 85% or more, 90% or more, 95% or more, 98% or more, or 99% or more. The higher the homology, the higher the possibility in which the properties of the mutant 2 are maintained in the further mutant, and thus the sufficient effects can be expected on the practical use.

Another specific example of the luciferase according to the embodiment is a luciferase having an amino acid sequence of SEQ ID NO: 42. In this amino acid sequence, substitutions of two amino acid residues are introduced into the amino acid sequence of SEQ ID NO: 38. The first substitution is the V256A as described above. The second substitution is a substitution in which an arginine residue at the 111th position from the N-terminal side in the amino acid sequence of SEQ ID NO: 38 is substituted by a histidine residue. This substitution mutation may be expressed as "R111H mutation" or "R111H" in the present application. The luciferase having the amino acid sequence of SEQ ID NO: 42 has mutations of R111H, S283G, and V256A, based on the amino acid sequence (SEQ ID NO: 1) of the wild type luciferase derived from *Luciora kuroiwae*. In the present application, the luciferase having the amino acid sequence of SEQ ID NO: 42 may be expressed as "mutant 3."

The mutant 3 has the following amino acid sequence:

```
                                           (SEQ ID NO: 42)
MEKEENVIYGPEPFYPVEEGSAGTQLHRFMERYAKMGAICFSNALTGQDV

TYAEYFDRSVRLAEALRRHGLTPEKKIGICSENCLEFFIPVLSGAYIASP

VAPTNEIYTIHELVHSFGISEPMIVFSSKKGLDKVLEVQKTVHSIKTIVI

IDSSTTYRGYDSMDAFVKKYVPANFNLSEFKTVEVDNETHTLLIMNSSGS

TGLPKGVLVRHCGAVTRFSHCRDPIFGNQVSPGTAILTVVPFHHGFGMFT

TLGYFACGYRIVMLTKFDDEVLLKTLQDYKCTGVILVPTLFAILNRSELL

EKFDLSNLTEIASGGAPLAKEVGEAVARRFNLPGVRQGYGLTETTSAFII

TPEGDDKPGASGKVVPLMKVKVIDLDTKKTLGPNRRGEICVKGPMLMTGY

EKNPTETKEIIDEDGWLHSGDIGYWDEDHHFFIVDRLKSLIKYKGYQVPP

AELESVLLQHPNIFDAGVAGIPDPEAGELPGAVVVLEKGKHLTEQEVLDY

VAGQVYNAKRLRGGVRFVDEVPKGLTGKIDAKAIREILKKPQAKM
```

Another specific example of the luciferase according to the embodiment is a further mutant having additional mutation(s) in the mutant 3 but maintaining the luminescence properties of the mutant 3. Specifically, the further mutant has an amino acid sequence which has 80% or more homology to the amino acid sequence of SEQ ID NO: 42 and which has a histidine residue, a glycine residue, and an alanine residue at the 111th, 283rd and 256th positions from the N-terminal side, respectively; the further mutant catalyzes a luminescence reaction generating luminescence having the maximum luminescent wavelength of 570 nm to 610 nm; and the luminescence has an intensity at least 10 times higher than that of luminescence generated in a luminescence reaction catalyzed by a luciferase having an amino acid sequence of SEQ ID NO: 48.

The homology between the amino acid sequence of the mutant 3 and the amino acid sequence of the further mutant of the mutant 3 is preferably 85% or more, 90% or more, 95% or more, 98% or more, or 99% or more. The higher the homology, the higher the possibility in which the properties of the mutant 3 are maintained in the further mutant, and thus the sufficient effects can be expected on the practical use.

The S283G mutant (mutant 1) may be excluded from the luciferase according to the embodiment.

The luciferase according to the embodiment can be used in an observation or quantification of the luminescence in vivo, as with the general luciferases. Further, the luciferase according to the embodiment can be used in a multicolor assay together with luciferase(s) capable of inducing luminescence having a color other than orange. In particular, it can be used in a three-color assay together with red luciferase and green luciferase.

A second embodiment of the present invention is a nucleic acid having a base sequence encoding the luciferase according to the embodiment.

The nucleic acid according to the embodiment may have a sequence in which the codon is optimized to a specific species. The "optimization" herein means that a codon of a gene contained in a nucleic acid is replaced by a codon having a high codon usage frequency in a specific species. When the optimization is performed, expression of the gene in the specific species is more increased compared to a case where the optimization is not performed. For example, the codon can be optimized to a mammal cell, specifically, a mouse or human cell.

The nucleic acid according to the embodiment may further contain a transcription factor-binding region such as a promoter, in addition to the base sequence of the luciferase.

The nucleic acid according to the embodiment may be in the form of a vector. This vector may contain a factor contained in a general vector, such as an antibiotic resistant gene or a replication origin, in addition to the gene encoding the luciferase according to the embodiment and the transcription factor-binding region such as the promoter.

One specific example of the nucleic acid according to the embodiment is a nucleic acid having a base sequence of SEQ ID NO: 41. The base sequence encodes the mutant 2.

The base sequence encoding the mutant 2 is as follow:

```
                                           (SEQ ID NO: 41)
ATGGAAAAAGAGGAAAACGTCATCTACGGCcCCGAGCCCTTCTACCCTGT

GGAAGAAGGCAGCGCCGGCACCCAGCTGCACCGGTTCATGGAAAGATACG

CCAAGATGGGCGCCATCTGCTTCAGCAATGCCCTGACCGGCCAGGACGTG
```

ACCTACGCCGAGTACTTCGACAGAAGCGTGCGGCTGGCCGAGGCCCTGAG

AAGGCATGGACTGACCCCCGAGAAGAAGATCGGCATCTGCAGCGAGAACT

GCCTGGAATTTTTCATCCCCGTGCTGAGCGGCGCCTATATCGCCTCTCCT

GTGGCCCCCACCAACGAGATCTACACCATCCGCGAGCTGGTGCACAGCTT

CGGCATCAGCGAGCCCATGATCGTGTTCAGCAGCAAGAAAGGCCTGGACA

AGGTGCTGGAAGTGCAGAAAACCGTGCACAGCATCAAGACCATCGTGATC

ATCGACAGCAGCACCACCTACCGGGGCTACGACAGCATGGACGCCTTCGT

GAAGAAATACGTGCCCGCCAACTTCAACCTGAGCGAGTTCAAGACCGTGG

AAGTGGACAACGAGACACACACCCTGCTGATCATGAACAGCTCCGGCAGC

ACCGGCCTGCCTAAAGGCGTGCTCGTCAGACATTGTGGCGCCGTGACCCG

GTTCAGCCACTGCAGAGATCCCATCTTCGGAAACCAGGTGTCCCCCGGCA

CCGCCATTCTGACCGTGGTGCCTTTCCACCACGGCTTCGGCATGTTCACC

ACCCTGGGCTACTTCGCGTGCGGCTACCGGATCGTGATGCTGACCAAGTT

CGACGACGAGGTGCTGCTGAAAACCCTGCAGGACTACAAGTGCACCGGCG

TGATCCTGGTGCCCACCCTGTTCGCCATCCTGAACAGAAGCGAGCTGCTG

GAAAAGTTCGACCTGAGCAATCTGACCGAGATTGCCTCTGGCGGAGCCCC

TCTGGCCAAAGAAGTGGGAGAAGCCGTCGCCAGACGGTTCAATCTGCCCG

GCGTGCGGCAGGGCTACGGACTGACTGAGACAACCAGCGCCTTCATCATC

ACACCCGAGGGCGACGATAAGCCTGGCGCCTCTGGAAAGGTGGTGCCCCT

GATGAAGGTCAAAGTGATCGACCTGGACACCAAGAAAACCCTGGGCCCCA

ACAGACGGGGCGAGATCTGTGTGAAGGGCCCCATGCTGATGACCGGCTAC

GAGAAGAACCCCACCGAGACAAAAGAGATCATCGACGAGGACGGCTGGCT

GCACTCTGGCGACATCGGCTACTGGGACGAGGACCACCACTTCTTCATCG

TGGACCGGCTGAAGTCCCTGATCAAGTACAAGGGCTACCAGGTGCCCCCT

GCCGAGCTGGAATCTGTGCTGCTGCAGCATCCCAACATCTTCGATGCCGG

CGTGGCCGGCATCCCTGATCCTGAAGCTGGCGAACTGCCAGGCGCTGTGG

TGGTGCTGGAAAAAGGCAAGCACCTGACAGAGCAGGAAGTGCTGGACTAC

GTCGCCGGCCAGGTGTACAACGCCAAGAGACTGAGAGGCGGCGTGCGCTT

CGTGGATGAAGTGCCTAAGGGCCTGACCGGCAAGATCGACGCCAAGGCCA

TCAGAGAGATCCTGAAGAAACCCCAGGCCAAGATGTGA

Another specific example of the nucleic acid according to the embodiment is a nucleic acid having a base sequence of SEQ ID NO: 43. This base sequence encodes the mutant 3.

The base sequence encoding the mutant 3 is as follow:

(SEQ ID NO: 43)
ATGGAAAAAGAGGAAAACGTCATCTACGGCCCCGAGCCCTTCTACCCTGT

GGAAGAAGGCAGCGCCGGCACCCAGCTGCACCGGTTCATGGAAAGATACG

CCAAGATGGGCGCCATCTGCTTCAGCAATGCCCTGACCGGCCAGGACGTG

ACCTACGCCGAGTACTTCGACAGAAGCGTGCGGCTGGCCGAGGCCCTGAG

AAGGCATGGACTGACCCCCGAGAAGAAGATCGGCATCTGCAGCGAGAACT

GCCTGGAATTTTTCATCCCCGTGCTGAGCGGCGCCTATATCGCCTCTCCT

GTGGCCCCCACCAACGAGATCTACACCATCCGCGAGCTGGTGCACAGCTT

CGGCATCAGCGAGCCCATGATCGTGTTCAGCAGCAAGAAAGGCCTGGACA

AGGTGCTGGAAGTGCAGAAAACCGTGCACAGCATCAAGACCATCGTGATC

ATCGACAGCAGCACCACCTACCGGGGCTACGACAGCATGGACGCCTTCGT

GAAGAAATACGTGCCCGCCAACTTCAACCTGAGCGAGTTCAAGACCGTGG

AAGTGGACAACGAGACACACACCCTGCTGATCATGAACAGCTCCGGCAGC

ACCGGCCTGCCTAAAGGCGTGCTCGTCAGACATTGTGGCGCCGTGACCCG

GTTCAGCCACTGCAGAGATCCCATCTTCGGAAACCAGGTGTCCCCCGGCA

CCGCCATTCTGACCGTGGTGCCTTTCCACCACGGCTTCGGCATGTTCACC

ACCCTGGGCTACTTCGCGTGCGGCTACCGGATCGTGATGCTGACCAAGTT

CGACGACGAGGTGCTGCTGAAAACCCTGCAGGACTACAAGTGCACCGGCG

TGATCCTGGTGCCCACCCTGTTCGCCATCCTGAACAGAAGCGAGCTGCTG

GAAAAGTTCGACCTGAGCAATCTGACCGAGATTGCCTCTGGCGGAGCCCC

TCTGGCCAAAGAAGTGGGAGAAGCCGTCGCCAGACGGTTCAATCTGCCCG

GCGTGCGGCAGGGCTACGGACTGACTGAGACAACCAGCGCCTTCATCATC

ACACCCGAGGGCGACGATAAGCCTGGCGCCTCTGGAAAGGTGGTGCCCCT

GATGAAGGTCAAAGTGATCGACCTGGACACCAAGAAAACCCTGGGCCCCA

ACAGACGGGGCGAGATCTGTGTGAAGGGCCCCATGCTGATGACCGGCTAC

GAGAAGAACCCCACCGAGACAAAAGAGATCATCGACGAGGACGGCTGGCT

GCACTCTGGCGACATCGGCTACTGGGACGAGGACCACCACTTCTTCATCG

TGGACCGGCTGAAGTCCCTGATCAAGTACAAGGGCTACCAGGTGCCCCCT

GCCGAGCTGGAATCTGTGCTGCTGCAGCATCCCAACATCTTCGATGCCGG

CGTGGCCGGCATCCCTGATCCTGAAGCTGGCGAACTGCCAGGCGCTGTGG

TGGTGCTGGAAAAAGGCAAGCACCTGACAGAGCAGGAAGTGCTGGACTAC

GTCGCCGGCCAGGTGTACAACGCCAAGAGACTGAGAGGCGGCGTGCGCTT

CGTGGATGAAGTGCCTAAGGGCCTGACCGGCAAGATCGACGCCAAGGCCA

TCAGAGAGATCCTGAAGAAACCCCAGGCCAAGATGTGA

A third embodiment of the present invention is a method for producing the luciferase according to the embodiment.

The method according to the embodiment includes a step of introducing a mutation into the gene of the mutant 1. For example, a mutation is introduced into a base sequence encoding the mutant 1 (SEQ ID NO: 39).

The base sequence encoding the mutant 1 is as follow:

(SEQ ID NO: 39)
ATGGAAAAAGAGGAAAACGTCATCTACGGCCCCGAGCCCTTCTACCCTGT

GGAAGAAGGCAGCGCCGGCACCCAGCTGCACCGGTTCATGGAAAGATACG

CCAAGATGGGCGCCATCTGCTTCAGCAATGCCCTGACCGGCCAGGACGTG

ACCTACGCCGAGTACTTCGACAGAAGCGTGCGGCTGGCCGAGGCCCTGAG

AAGGCATGGACTGACCCCCGAGAAGAAGATCGGCATCTGCAGCGAGAACT

GCCTGGAATTTTTCATCCCCGTGCTGAGCGGCGCCTATATCGCCTCTCCT

GTGGCCCCCACCAACGAGATCTACACCATCCGCGAGCTGGTGCACAGCTT

CGGCATCAGCGAGCCCATGATCGTGTTCAGCAGCAAGAAAGGCCTGGACA

-continued

```
AGGTGCTGGAAGTGCAGAAAACCGTGCACAGCATCAAGACCATCGTGATC

ATCGACAGCAGCACCACCTACCGGGGCTACGACAGCATGGACGCCTTCGT

GAAGAAATACGTGCCCGCCAACTTCAACCTGAGCGAGTTCAAGACCGTGG

AAGTGGACAACGAGACACACACCCTGCTGATCATGAACAGCTCCGGCAGC

ACCGGCCTGCCTAAAGGCGTGCTCGTCAGACATTGTGGCGCCGTGACCCG

GTTCAGCCACTGCAGAGATCCCATCTTCGGAAACCAGGTGTCCCCCGGCA

CCGCCATTCTGACCGTGGTGCCTTTCCACCACGGCTTCGGCATGTTCACC

ACCCTGGGCTACTTCGTGTGCGGCTACCGGATCGTGATGCTGACCAAGTT

CGACGACGAGGTGCTGCTGAAAACCCTGCAGGACTACAAGTGCACCGGCG

TGATCCTGGTGCCCACCCTGTTCGCCATCCTGAACAGAAGCGAGCTGCTG

GAAAAGTTCGACCTGAGCAACCTGACCGAGATCGCCTCTGGCGGAGCCCC

TCTGGCCAAAGAAGTGGGAGAAGCCGTCGCCAGACGGTTCAATCTGCCCG

GCGTGCGGCAGGGCTACGGACTGACAGAGACAACCAGCGCCTTCATCATC

ACCCCCGAGGGCGACGATAAGCCTGGCGCCTCTGGAAAGGTGGTGCCCCT

GATGAAGGTCAAAGTGATCGACCTGGACACCAAGAAAACCCTGGGCCCCA

ACAGACGGGCGAGATCTGTGTGAAGGGCCCCATGCTGATGACCGGCTAC

GAGAAGAACCCCACCGAGACAAAAGAGATCATCGACGAGGACGGCTGGCT

GCACTCTGGCGACATCGGCTACTGGGACGAGGACCACCACTTCTTCATCG

TGGACCGGCTGAAGTCCCTGATCAAGTACAAGGGCTACCAGGTGCCCCCT

GCCGAGCTGGAATCTGTGCTGCTGCAGCATCCCAACATCTTCGATGCCGG

CGTGGCCGGCATCCCTGATCCTGAAGCTGGCGAACTGCCAGGCGCTGTGG

TGGTGCTGGAAAAAGGCAAGCACCTGACAGAGCAGGAAGTGCTGGACTAC

GTCGCCGGCCAGGTGTACAACGCCAAGAGACTGAGAGGCGGCGTGCGCTT

CGTGGATGAAGTGCCTAAGGGCCTGACCGGCAAGATCGACGCCAAGGCCA

TCAGAGAGATCCTGAAGAAACCCCAGGCCAAGATGTGA
```

The mutation may be introduced in a general method. For example, the mutation may be randomly introduced by utilizing a mutagen such as nitrosoguanidine or ultraviolet rays. Alternatively, the mutation may be randomly introduced in a PCR method by using a DNA polymerase which induces mutation at a fixed frequency. Alternatively, the mutation may be introduced into a specific position using a gene recombination technique or the like.

The method according to the embodiment includes a step of selecting a desired mutant from candidate mutants, after the step of introducing the mutation.

The selection may be performed in a general screening technology. Specifically, for example, the mutation-introduced nucleic acid is inserted into an expression vector, and the obtained vector is incorporated into *E. coli* to express the mutant gene in the *E. coli*. After that, a substance necessary for the luminescence reaction, such as a luciferin, is added thereto to cause the luminescence reaction. From a luminescence state, *E. coli* expressing the luciferase according to the embodiment, i.e., *E. coli* showing orange luminescence at a high brightness, can be selected. After that, nucleic acids containing the luciferase gene may be extracted from the selected *E. coli*, or a base sequence of the gene may be confirmed.

According to the embodiments described above, the following effects are obtained.

According to the embodiments of the present invention, the orange luminescence can be realized at a high brightness.

Hitherto, when a chemiluminescent sample having a low luminescence intensity is photographed by using a microscope, an exposure time necessary for capturing a clear image has been prolonged. Applicable research uses of such a chemiluminescent sample are restricted. For example, when an exposure time of 30 minutes is necessary due to a low luminescence intensity, it is possible to perform photographing in 30-minute intervals, but it is impossible to perform photographing in a shorter time interval, particularly, real-time photographing. Further, in the capturing of an image, it is necessary that multiple images are captured and compared in order to focus on the cell that emits light. Therefore, when a long exposure time is necessary due to the low luminescence intensity, time and labor are necessary in order to capture only one image.

In contrast, the luciferase according to the embodiment can cause the orange luminescence having a higher brightness, compared to the already-known luciferase, and thus it exhibits particularly advantageous effects when it is used as a reporter for imaging a protein. Specifically, the luciferase according to the embodiment can provide a high luminescence intensity even in a small amount, and thus a protein having a low level of expression can be excellently detected. In addition, the luminescence intensity obtained by the luciferase is high, and thus an exposure time necessary for detection can be shortened. For these reasons, when this luciferase is used as a reporter for a time-lapse observation, it is possible to shorten the exposure time necessary for the photographing, which enables an observation closer to the real-time observation. In other words, it enables a time-lapse observation having a high temporal resolution.

In addition, orange luminescence having a sufficient luminescence intensity has not been obtained from the conventional luciferases generating the orange luminescence. In the first place, the number of the luciferases generating the orange luminescence is small. For that reason, the conventional multicolor assay of red, orange and green has a low utility.

On the other hand, the luciferase of the embodiment can generate the orange luminescence having the high brightness. Therefore, when the luciferase is used in the multicolor assay of red, orange and green, separation from signals of other luciferases is improved, which enables a measurement having a high quantitativity.

EXAMPLES

Example 1: Cloning of Luciferase Gene Derived from *Luciora kuroiwae*

1. Material

Four imagoes of *Luciora kuroiwae*, from Kumejima Island, Okinawa Prefecture, Japan, were used as a material.

2. Extraction of Total RNA and Synthesis of cDNA

Luminous organs were taken out from the imagoes of the firefly with scissors. The luminous organ taken out and 1 mL of total RNA extraction reagent, TRIzol Reagent (Invitrogen Inc.) were put in a Lysing Matrix D tube (MP-Biomedicals Inc.) which is a tube containing beads for homogenizing tissues and cells. This tube is equipped to a tissue/cell disrupter, FastPrep 24 (MP-Biomedicals Inc.) or FastPrep FP100A (MP-Biomedicals Inc.), and the luminous organ of the firefly was disrupted in the reagent at conditions of a vibration velocity of 6.5 m/second and a vibration time of 45 seconds. After that, the tube was taken out from the disrupter, and it was put on ice over 30 minutes. After that, the disruption was performed again in the same conditions as above.

Next, separation and purification of the total RNA were performed from the solution obtained by the disruption, according to the manual of the total RNA extraction reagent, TRIzol Reagent. 100 µl of the obtained RNA solution was precipitated and concentrated by an ethanol precipitation method. Next, a full length cDNA synthesizing reagent, GeneRacer (Invitrogen Inc.) was used according to the manual to synthesize a full length cDNA from the total RNA obtained by the precipitation and concentration. 20 µl of the obtained cDNA solution was used in the following gene experiments as a firefly full length cDNA library.

3. Identification of 5'-Terminal Side of Firefly Luciferase Gene 3-1. Preparation of Primer Using Rapid Amplification of cDNA End (RACE) Method Cloning of the luciferase gene of *Luciora kuroiwae* was performed by a Polymerase chain reaction (PCR) method. A primer used in this PCR was prepared in the following method based on an amino acid sequence of a luciferase gene derived from already-known related species.

In order to confirm an amino acid region well conserved in the firefly luciferase, amino acid sequences of 10 kinds of firefly luciferases, which have been already published, were compared using a sequence information analyzing software, DNASIS Pro (Hitachi Software Engineering Co., Ltd.). The related species used for the comparison are: *Lampyris noctiluca* (Registration No. CAA61668), *Luciola cruciata* (Registration No. P13129), *Luciola lateralis* (Registration No. Q01158), *Luciola mingrelica* (Registration No. Q26304), *Hotaria parvula* (Registration No. AAC37253), *Photinus pyralis* (Registration No. BAF48390), *Photuris pennsylvanica* (Registration No. Q27757), *Pyrocoelia miyako* (Registration No. AAC37254), *Pyrocoelia rufa* (Registration No. AAG45439), and *Rhagophthalmus ohbai* (Registration No. BAF34360).

As a result, it was revealed that the amino acid sequence of L-I-K-Y-K-G-Y-Q-V (SEQ ID NO: 7), located at around the 440th residue on the C-terminal side of the firefly luciferase, was well conserved. Base sequences were predicted from codons encoding the sequence of 9 amino acids, and 12 types of mixed primers specific to firefly luciferase were designed for use in 5'-terminal RACE PCR. The names and sequences of the primers are described below (Y, R and N in the primer sequences represent mixed bases. Specifically, Y represents C or T, R represents A or G, and N represents A, G, C, or T).

flexLuc5-ATA (5'-ACY TGR TAN CCY TTA TAT TTA AT-3': SEQ ID NO: 8),
flexLuc5-ATG (5'-ACY TGR TAN CCY TTA TAT TTG AT-3': SEQ ID NO: 9),
flexLuc5-ATT (5'-ACY TGR TAN CCY TTA TAT TTT AT-3': SEQ ID NO: 10),
flexLuc5-ACA (5'-ACY TGR TAN CCY TTA TAC TTA AT-3': SEQ ID NO: 11),
flexLuc5-ACG (5'-ACY TGR TAN CCY TTA TAC TTG AT-3': SEQ ID NO: 12),
flexLuc5-ACT (5'-ACY TGR TAN CCY TTA TAC TTT AT-3': SEQ ID NO: 13),
flexLuc5-GTA (5'-ACY TGR TAN CCY TTG TAT TTA AT-3': SEQ ID NO: 14),
flexLuc5-GTG (5'-ACY TGR TAN CCY TTG TAT TTG AT-3': SEQ ID NO: 15),
flexLuc5-GTT (5'-ACY TGR TAN CCY TTG TAT TTT AT-3': SEQ ID NO: 16),
flexLuc5-GCA (5'-ACY TGR TAN CCY TTG TAC TTA AT-3': SEQ ID NO: 17),
flexLuc5-GCG (5'-ACY TGR TAN CCY TTG TAC TTG AT-3': SEQ ID NO: 18), and
flexLuc5-GCT (5'-ACY TGR TAN CCY TTG TAC TTT AT-3': SEQ ID NO: 19). The primers were synthesized consigning to Life Technologies Japan Co. Ltd.

3-2. Cloning of 5'-Terminal Side of Firefly Luciferase Gene by 5'-RACE PCR

5'-RACE PCR was performed using the firefly full length cDNA library prepared as above, as a template, and using the 12 types of mixed primers prepared as above, and 5'-terminal specific primers, GeneRacer 5' Primer (5'-CGA CTG GAG CAC GAG GAC ACT GA-3': SEQ ID NO: 20) and GeneRacer 5' Nested Primer (5'-GGA CAC TGA CAT GGA CTG AAG GAG TA-3': SEQ ID NO: 21). As the GeneRacer 5' Primer and GeneRacer 5' Nested Primer, those contained in a full length cDNA synthetic reagent GeneRacer kit (Invitrogen Inc.) were used. In order to efficiently amplify the luciferase gene by the 5'-RACE PCR, a nested PCR was performed in which a gene was more specifically amplified using a gene which had once been amplified by PCR, as a template, and using an inner primer pair. The PCR was performed using polymerase Ex-Taq (Takara Bio Inc.) according to the manual.

In a first PCR, the luciferase gene was amplified using 12 types of primer pairs consisting of the 12 types of mixed primers prepared as above, and the GeneRacer 5' Primer. 10 µl of a PCR reaction solution containing 10×Ex Taq Buffer (20 mM Mg2+ plus) having a final concentration of tenfold dilution, dNTP Mixture (each 2.5 mM) having each final concentration of 0.2 mM, TaKaRa Ex Taq (5 U/µl) having a final concentration of 0.05 U/µl, one of 12 types of primers having a final concentration of 1.0 µM, and GeneRacer 3' Primer having a final concentration of 0.3 µM was prepared. 0.2 µl of the firefly full length cDNA library solution was added to the prepared PCR reaction solution. The concentration of the firefly full length cDNA library solution was not quantified. The PCR reaction was performed by first performing thermal denaturation at 94° C. for 2 minutes, then repeating 30 times a cycle consisting of 94° C. for 30 seconds, 45° C. for 30 seconds, and 72° C. for 90 seconds, and finally performing an elongation reaction at 72° C. for 5 minutes. After the PCR reaction, 1 µl of the PCR reaction solution was subjected to electrophoresis using 1% trisacetate buffer (TAE) agarose gel and stained with ethidium bromide, and then bands of the amplified gene were observed under ultraviolet-ray irradiation. Gene amplification was slightly observed in the all of the 12 reaction solutions, and thus the nested PCR reaction was performed using each of the PCR reaction solution as a template as shown below.

In the nested PCR, the luciferase gene was amplified using 4 types of primer pairs consisting of the 4 types of primers selected from the 12 types of primers used in the first PCR, and GeneRacer 3' Nested Primer. 10 µl of a PCR reaction solution containing 10×Ex Tag Buffer (20 mM Mg2+ plus) having a final concentration of tenfold dilution, dNTP Mixture (each 2.5 mM) having each final concentration of 0.2 mM, TaKaRa Ex Tag (5 U/µl) having a final concentration of 0.05 U/µl, one of 12 types of primers having a final concentration of 1.0 µM, and GeneRacer 3' Primer having a final concentration of 0.3 µM was prepared. The first PCR reaction solution was diluted with sterilized water by 10 times, and 1.0 µl of the diluted solution was added as a template to the prepared PCR reaction solution. The PCR reaction was performed by first performing thermal denaturation at 94° C. for 2 minutes, then repeating 30 times a cycle consisting of 94° C. for 30 seconds, 45° C. for 30 seconds, and 72° C. for 90 seconds, and finally performing an elongation reaction at 72° C. for 5 minutes. After the PCR reaction, 1 µl of the PCR reaction solution was subjected to electrophoresis using 1% TAE agarose gel and stained with ethidium bromide, and then bands of the amplified gene were observed under ultraviolet-ray irradiation. A primer pair which enabled an efficient gene amplification at a size of about 1.4 kbp was confirmed.

3-3. Determination of Base Sequence of Gene Amplified by 5'-RACE

In order to read a base sequence of the gene amplified by the 5'-RACE, purification of the PCR product through a gel extraction, subcloning, and direct sequencing were performed. The details are shown below.

PCR (a final volume: 20 µl) was performed using the primer pair which enabled the efficient gene amplification at a size of about 1.4 kbp, and desired gene fragments were collected using a gel extraction method. The gel extraction was performed using Wizard SV Gel and PCR Clean-Up System (Promega KK.) according to the manual. The subcloning of the PCR product extracted from the gel was performed using a TA cloning method. The TA cloning was performed using pGEM-T Easy Vector System (Promega KK.) according to the manual. After that, the vector DNA was transformed into *E. coli* (TOP10 strain or DH5α strain), and an insert positive colony was selected using a blue-white screening method. The selected colony was subjected to a direct colony PCR, whereby it was confirmed that the gene was transferred. In the direct colony PCR, a primer pair consisting of M13-F(-29) Primer (5'-CAC GAC GTT GTA AAA CGA C-3': SEQ ID NO: 22) and M13 Reverse (5'-GGA TAA CAA TTT CAC AGG-3': SEQ ID NO: 23) was used. 10 µl of a PCR reaction solution containing 10×Ex Taq Buffer (20 mM Mg2+ plus) having a final concentration of tenfold dilution, dNTP Mixture (each 2.5 mM) having each final concentration of 0.2 mM, TaKaRa Ex Taq (5 U/µl) having a final concentration of 0.05 U/µl, and the primer pair having each final concentration of 0.2 µM was prepared. A small amount of the *E. coli* colony was added as a template to the prepared PCR reaction solution. The PCR reaction was performed by first performing thermal denaturation at 94° C. for one minute, then repeating 25 times a cycle consisting of 94° C. for 30 seconds, 50° C. for 30 seconds, and 72° C. for 2 minutes, and finally performing an elongation reaction at 72° C. for 2 minutes. After the PCR reaction, 2 µl of the PCR reaction solution was subjected to electrophoresis using 1% TAE agarose gel and stained with ethidium bromide, and then bands of the amplified gene were observed under ultraviolet-ray irradiation.

In the PCR reaction solution in which the gene amplification was confirmed, a base sequence of the gene was determined using a direct sequencing method. The extra dNTP and primers contained in the PCR reaction solution were removed using a PCR product purification kit, ExoSAP-IT (GE Healthcare Biosciences K.K.), whereby a template for PCR direct sequencing was prepared. A sequencing reaction solution containing the template was prepared using BigDye Terminator v3.1 Cycle Sequencing Kit (Applied Biosystems), and a sequencing reaction was performed using a thermal cycler. The purification and sequencing of the PCR product were performed according to the manuals. After the sequencing reaction, purification of the reaction product was performed as follows. To the reaction solution was added 100% ethanol in an amount of 2.5 times, and nucleic acids were precipitated using a centrifuge. Next, after the supernatant was removed, the precipitates were washed by adding 70% ethanol thereto, and the nucleic acids were precipitated using the centrifuge. Finally, after a supernatant was removed, the precipitates were dried. To the purified precipitates was added 15 µl of Hi-Di Formamide (Applied Biosystems) to lyse them. The resulting solution was subjected to thermal denaturation at 94° C. for 2 minutes, and quickly cooled on ice, whereby a sample for determining a base sequence was obtained. A base sequence of the sample was read using an Applied Biosystems 3130xl genetic analyzer (Applied Biosystems). The analysis method of the base sequence was performed according to the manual. The obtained base sequence was determined as a base sequence of a 5'-terminal side untranslated region of *Luciora kuroiwae* luciferase gene. The sequence is as follow:

```
                                           (SEQ ID NO: 24)
GTTCGGTATACTCGCGAGTTCGGGCAAAAAATAACAAGTAGCGCAAGATG

GAAAAAGAAGAAAATGTGATATACGGTCCCGAGCCGTTTTACCCCGTCGA

AGAGGGATCTGCAGGAACGCAACTGCACAGATTTATGGAGCGATACGCCA

AAATGGGGCTATATGTTTTTCTAACGCCCTCACGGGCCAAGATGTAACG

TATGCCGAATATTTTGACCGACCGGTTCGTTTAGCGGAAGCTTTGAGAAG

GCACGGCTTAACGCCAGAGAAAAAAATCGGTATTTGCAGCGAAAATTGCT

TAGAATTTTTCATTCCGGTGCTTTCGGGAGCGTATATCGCTTCACCCGTC

GCTCCAACTAACGAAATTTACACTATACGCGAATTGGTTCACAGTTTTGG

AATATCCGAGCCAATGATCGTGTTTAGCTCAAAGAAAGGATTGGATAAAG

TCTTGGAAGTACAAAAACAGTGCACTCTATTAAAACAATAGTCATTATT

GATAGCTCAACTACTTATCGAGGATATGACAGCATGGATGCGTTTGTTAA

AAAAATACGTACCCGCAAATTTCAATTTATCCGAATTCAAAACTGTAGAA

GTCGATAATGAAACTCACACTCTTCTTATAATGAACTCGTCCGGTTCCAC

CGG
```

The gene sequence obtained by the sequencing was analyzed by using a "sequence linking" function of a sequence information analysis software, DNASIS Pro. The sequence was subjected to a homology search utilizing a blastx search, provided by National Center for Biotechnology Information (NCBI), and it was confirmed that the sequence had a high homology to the base sequence of an already-known firefly luciferase. The base sequence obtained by the experiment and analysis described above was determined as the 5'-terminal side of the novel firefly luciferase gene.

4. 3'Race PCR of Firefly Luciferase Gene and Obtaining of Full Length cDNA 4-1. Design of Primer for Use in 3'Race PCR A primer (SEQ ID NO: 27) for use in 3'RACE, and a primer (SEQ ID NO: 28) for use in Nested PCR were prepared base on the sequence of the 5'-terminal side untranslated region of the firefly luciferase gene, which was obtained in the 5'Race PCR experiment. The primers were synthesized consigning to Life Technologies Japan Co. Ltd.

4-2. 3'Race PCR for Obtaining of Full Length cDNA of Firefly Luciferase Gene

3'-RACE PCR was performed using the firefly full length cDNA library prepared as above, as a template, and using primers consisting of a primer No2-Kuroiwa-F1 (GTTCGGTATACTCGCGAGTTCG: SEQ ID NO: 25), which was prepared from the base sequence of the 5'-terminal side untranslated region of the object firefly luciferase, GeneRacer 3' Primer (5'-GCT GTC AAC GAT ACG CTA CGT AAC G-3': SEQ ID NO: 27), and GeneRacer 3' Nested Primer (5'-CGC TAC GTA ACG GCA TGA CAG TG-3': SEQ ID NO: 28). As the GeneRacer 3' Primer and GeneRacer 3' Nested Primer, those contained in a full length cDNA synthetic reagent GeneRacer kit (Invitrogen Inc.) were used. In order to efficiently amplify the luciferase gene by the 3'-RACE PCR, a nested PCR was performed in which a gene was more specifically amplified using a gene which had once been amplified by PCR, as a template, and using an inner primer pair. The PCR was performed according using polymerase Ex-Taq (Takara Bio Inc.) to the manual.

In a first PCR, the luciferase gene was amplified using a primer pair consisting of a primer prepared from the base sequence of the 5'-terminal side untranslated region, and the GeneRacer 3' Primer. 20 µl of a PCR reaction solution containing 10×Ex Taq Buffer (20 mM Mg2+ plus) having a final concentration of tenfold dilution, dNTP Mixture (each 2.5 mM) having each final concentration of 0.2 mM, TaKaRa Ex Taq (5 U/µl) having a final concentration of 0.05 U/µl, and primers having each final concentration of 0.3 µM was prepared. 0.4 µl of the firefly full length cDNA library solution was added to the prepared PCR reaction solution. The concentration of the firefly full length cDNA library solution was not quantified. The PCR reaction was performed by first performing thermal denaturation at 94° C. for 2 minutes, then repeating 30 times a cycle consisting of 94° C. for 30 seconds, 50° C. for 30 seconds, and 72° C. for 2 minutes, and finally performing an elongation reaction at 72° C. for 5 minutes. After the PCR reaction, 1 µl of the PCR reaction solution was subjected to electrophoresis using 1% TAE agarose gel and stained with ethidium bromide, and then bands of the amplified gene were observed under ultraviolet-ray irradiation. Gene amplification was slightly observed, and thus the nested PCR reaction was performed using the PCR reaction solution as a template.

In the Nested PCR, the luciferase gene was amplified using a primer pair consisting of a primer No2-Kuroiwa-F2 for Nested PCR (GTTCGGTATACTCGCGAGT-TCGGGCAA: SEQ ID NO: 26), and GeneRacer 3' Nested Primer. 20 µl of an nested PCR reaction solution containing 10×Ex Taq Buffer (20 mM Mg2+ plus) having a final concentration of tenfold dilution, dNTP Mixture (each 2.5 mM) having each final concentration of 0.2 mM, TaKaRa Ex Taq (5 U/µl) having a final concentration of 0.05 U/µl, and primers having each final concentration of 0.3 µM was prepared. The first PCR reaction solution was diluted with sterilized water by 10 times, and 1.0 µl of the diluted solution was added as a template to the prepared nested PCR reaction solution. The PCR reaction was performed by first performing thermal denaturation at 94° C. for 2 minutes, then repeating 30 times a cycle consisting of 94° C. for 30 seconds, 50° C. for 30 seconds, and 72° C. for 2 minutes, and finally performing an elongation reaction at 72° C. for 5 minutes. After the PCR reaction, 1 µl of the PCR reaction solution was subjected to electrophoresis using 1% TAE agarose gel and stained with ethidium bromide, and then bands of the amplified gene were observed under ultraviolet-ray irradiation. It was confirmed that the gene was efficiently amplified at a size of about 2 kbp.

4-3. Determination of Base Sequence of Gene Amplified by 3'-Race

In order to read a base sequence of the gene amplified by the 3'-RACE, purification of the PCR product through a gel extraction, subcloning, and direct sequencing were performed. The details are shown below.

PCR (a final volume: 20 µl) was performed using the primer pair which enabled the efficient gene amplification at a size of about 2 kbp, and desired gene fragments were collected using a gel extraction method. The gel extraction was performed using Wizard SV Gel and PCR Clean-Up System (Promega KK.) according to the manual. The subcloning of the PCR product extracted from the gel was performed using a TA cloning method. The TA cloning was performed using pGEM-T Easy Vector System (Promega KK.) according to the manual. After that, the vector DNA was transformed into E. coli (TOP10 strain or DH5α strain), and an insert positive colony was selected using a blue-white screening method. The selected colony was subjected to a direct colony PCR, whereby it was confirmed that the gene was transferred. In the direct colony PCR, a primer pair consisting of M13-F(-29) Primer (5'-CAC GAC GTT GTA AAA CGA C-3': SEQ ID NO: 22) and M13 Reverse (5'-GGA TAA CAA TTT CAC AGG-3': SEQ ID NO: 23) was used. 10 µl of a PCR reaction solution containing 10×Ex Taq Buffer (20 mM Mg2+ plus) having a final concentration of tenfold dilution, dNTP Mixture (each 2.5 mM) having each final concentration of 0.2 mM, TaKaRa Ex Taq (5 U/µl) having a final concentration of 0.05 U/µl, and the primer pair having each final concentration of 0.2 µM was prepared. A small amount of the E. coli colony was added as a template to the prepared PCR reaction solution. The PCR reaction was performed by first performing thermal denaturation at 94° C. for one minute, then repeating 25 times a cycle consisting of 94° C. for 30 seconds, 50° C. for 30 seconds, and 72° C. for 2 minutes, and finally performing an elongation reaction at 72° C. for 2 minutes. After the PCR reaction, 2 µl of the PCR reaction solution was subjected to electrophoresis using 1% TAE agarose gel and stained with ethidium bromide, and then bands of the amplified gene were observed under ultraviolet-ray irradiation.

In the PCR reaction solution in which the gene amplification was confirmed, a base sequence of the gene was determined using a direct sequencing method. The extra dNTP and primers contained in the PCR reaction solution were removed using a PCR product purification kit, ExoSAP-IT (GE Healthcare Biosciences K.K.), whereby a template for PCR direct sequencing was prepared. A sequencing reaction solution containing the template was prepared using BigDye Terminator v3.1 Cycle Sequencing Kit (Applied Biosystems), and a sequencing reaction was performed using a thermal cycler. As the primer used in the sequencing, a vector primer or gene-specific primer was used. The purification and sequencing of the PCR product were performed according to the manuals. After the sequencing reaction, purification of the reaction product was performed as follows. To the reaction solution was added 100% ethanol in an amount of 2.5 times, and nucleic acids were precipitated in a centrifuge. Next, after the supernatant was removed, the precipitates were washed by adding 70% ethanol thereto, and the nucleic acids were precipitated in the centrifuge. Finally, after a supernatant was removed, the precipitates were dried. To the purified precipitates was added 15 µl of Hi-Di Formamide (Applied Biosystems) to lyse them. The resulting solution was subjected to thermal denaturation at 94° C. for 2 minutes, and quickly cooled on ice, whereby a sample for determining a base sequence was obtained. A base sequence of the sample was read using an Applied Biosystems 3130xl genetic analyzer (Applied Biosystems). The analysis method of the base sequence was performed according to the manual. The base sequence determined by the sequencing is represented by SEQ ID NO: 44. A base sequence from an initiation codon to a termination codon in SEQ ID NO: 44 was determined as a base sequence of the wild type *Luciora kuroiwae* luciferase gene. The base sequence of the wild type *Luciora kuroiwae* luciferase gene is as follow:

(SEQ ID NO: 2)
ATGGAAAAGAAGAAAATGTGATATACGGTCCCGAGCCGTTTTACCCGT

CGAAGAGGGATCTGCAGGAACGCAACTGCACAGATTTATGGAGCGATACG

CCAAAATGGGGCTATATGTTTTTCTAACGCCCTCACGGGCCAAGATGTA

ACGTATGCCGAATATTTTGACCGATCGGTTCGTTTAGCGGAAGCTTTGAG

AAGGCACGGCTTAACGCCAGAGAAAAAAATCGGTATTTGCAGCGAAAATT

GCTTAGAATTTTTCATTCCGGTGCTTTCGGGAGCGTATATCGCTTCACCC

GTCGCTCCAACTAACGAAATTTACACTATACGCGAATTGGTTCACAGTTT

TGGAATATCCGAGCCAATGATCGTGTTTAGCTCAAAGAAAGGATTGGATA

AAGTCTTGGAAGTACAAAAAACAGTGCACTCTATTAAAACAATAGTCATT

ATTGATAGCTCAACTACTTATCGAGGATATGACAGCATGGATGCGTTTGT

TAAAAAATACGTACCCGCAAATTTCAATTTATCCGAATTCAAAACTGTAG

AAGTCGATAATGAAACTCACACTCTTCTTATAATGAACTCGTCCGGTTCC

ACCGGTCTACCGAAAGGTGTGCTAGTCCGTCATTGTGGGCAGTTACAAG

ATTTTCTCATTGCAGGGATCCGATTTTTGGTAATCAAGTTTCACCAGGCA

CAGCAATTTTAACGGTCGTTCCGTTCCATCATGGCTTTGGTATGTTCACT

ACTTTAGGATACTTTGTTTGTGGATACCGAATCGTAATGTTAACAAAATT

TGATGACGAAGTATTGTTGAAAACCCTACAAGATTATAAGTGTACTAGTG

TTATCCTAGTACCAACTTTGTTCGCTATCCTTAATAGAAGTGAACTACTG

GAGAAATTCGACTTGTCTAATCTGACTGAAATTGCATCTGGTGGTGCCCC

ATTAGCAAAAGAAGTTGGGGAAGCCGTTGCCAGAAGATTTAATCTTCCTG

GTGTTCGCCAAGGTTACGGTTTAACTGAAACCACATCCGCTTTTATTATC

ACCCCAGAAGGGGATGACAAACCAGGGGCTTCTGGAAAAGTTGTGCCTTT

AATGAAAGTTAAAGTGATTGATCTTGACACTAAGAAAACGCTTGGTCCTA

ACCGTCGTGGAGAAATTTGCGTTAAGGGTCCTATGTTGATGACAGGTTAC

GAGAAGAATCCTACAGAAACTAAAGAAATTATCGACGAAGATGGTTGGCT

GCACAGTGGAGATATTGGGTATTGGGACGAAGATCATCACTTCTTTATTG

TAGATCGTCTCAAATCCTTAATCAAATACAAAGGATATCAAGTACCACCT

GCTGAATTGGAATCCGTACTTTTACAACATCCAAATATATTTGATGCCGG

TGTTGCCGGAATTCCCGATCCCGAAGCCGGGGAGCTTCCGGGTGCTGTGG

TTGTATTAGAGAAAGGAAAACATCTAACTGAACAAGAAGTATTGGATTAC

GTTGCCGGACAAGTTTACAACGCAAAACGTTTACGCGGTGGCGTTCGTTT

TGTAGACGAGGTACCTAAAGGTCTCACTGGAAAAATTGACGCAAAGGCAA

TTAGAGAAATTCTTAAGAAGCCGCAAGCTAAGATGTGA

The full length firefly luciferase gene was obtained by the sequencing. A homology search of each of the base sequence (SEQ ID NO: 2) and its amino acid translated sequence (SEQ ID NO: 1) was performed utilizing blastx and blastp searches, provided by NCBI. In each search, it was confirmed that the sequence had a high homology to the base sequence or amino acid sequence of an already-known firefly luciferase. The base sequence obtained by the experiment and analysis described above was determined as the full length cDNA sequence of the wild type *Luciora kuroiwae* luciferase gene.

Hereinafter, the protein encoded by the luciferase gene was referred to as a wild type *Luciora kuroiwae* luciferase.

In order to confirm whether the amino acid sequence (SEQ ID NO: 1) obtained by translating the base sequence of SEQ ID NO: 2 showed the luminescence activity as the luciferase, the following experiment was performed.

According to the base sequence determined as above, the wild type *Luciora kuroiwae* luciferase gene contains recognition sequences of restriction enzymes EcoRI and BamHI. A genetic modification was performed, in which the recognition sequences were removed while maintaining the amino acid sequence of the luciferase. The modification was performed in order to facilitate the introduction of the luciferase gene into an expression vector, as described below. The introduction of the gene mutation was performed using primers of SEQ ID NOS: 45, 46 and 47 according to a molecular biological genetic modification. The mutation-introduced sequence is a base sequence represented by SEQ ID NO: 3. The base sequence of SEQ ID NO: 3 does not contain recognition sequences of restriction enzymes EcoRI and BamHI. In order to express the base sequence of SEQ ID NO: 3 in *E. coli*, the base sequence of SEQ ID NO: 3 was introduced to a pRSET-B vector (Invitrogen Com.) using a primer pair (SEQ ID NOS: 29 and 30) for introducing a gene into a vector containing the recognition sequences of the restriction enzymes EcoRI and BamHI. The obtained vector DNA was transformed into *E. coli* JM109 (DE3) strains, thereby forming colonies. Using the primer pair of SEQ ID NOS: 31 and 32, it was confirmed whether the gene was normally transferred to the colonies. The luminescence was observed by spraying a D-Luciferin containing solution to the colonies to which the gene was normally transferred.

Example 2: Preparation of S283G Mutant *Luciora kuroiwae* Luciferase

A mutant gene expressing S283G mutant *Luciora kuroiwae* luciferase was prepared as described below.

The base sequence (SEQ ID NO: 2) of the wild type *Luciora kuroiwae* luciferase gene prepared in Example 1 was optimized for the expression in a mammalian cell. The optimized base sequence is as follow:

(SEQ ID NO: 4)
ATGGAAAAAGAGGAAAACGTCATCTACGGCCCCGAGCCCTTCTACCCTGT

GGAAGAAGGCAGCGCCGGCACCCAGCTGCACCGGTTCATGGAAAGATACG

CCAAGATGGGCGCCATCTGCTTCAGCAATGCCCTGACCGGCCAGGACGTG

ACCTACGCCGAGTACTTCGACAGAAGCGTGCGGCTGGCCGAGGCCCTGAG

AAGGCATGGACTGACCCCCGAGAAGAAGATCGGCATCTGCAGCGAGAACT

GCCTGGAATTTTTCATCCCCGTGCTGAGCGGCGCCTATATCGCCTCTCCT

GTGGCCCCCACCAACGAGATCTACACCATCCGCGAGCTGGTGCACAGCTT

CGGCATCAGCGAGCCCATGATCGTGTTCAGCAGCAAGAAAGGCCTGGACA

AGGTGCTGGAAGTGCAGAAAACCGTGCACAGCATCAAGACCATCGTGATC

ATCGACAGCAGCACCACCTACCGGGGCTACGACAGCATGGACGCCTTCGT

-continued
```
GAAGAAATACGTGCCCGCCAACTTCAACCTGAGCGAGTTCAAGACCGTGG

AAGTGGACAACGAGACACACACCCTGCTGATCATGAACAGCTCCGGCAGC

ACCGGCCTGCCTAAAGGCGTGCTCGTCAGACATTGTGGCGCCGTGACCCG

GTTCAGCCACTGCAGAGATCCCATCTTCGGAAACCAGGTGTCCCCCGGCA

CCGCCATTCTGACCGTGGTGCCTTTCCACCACGGCTTCGGCATGTTCACC

ACCCTGGGCTACTTCGTGTGCGGCTACCGGATCGTGATGCTGACCAAGTT

CGACGACGAGGTGCTGCTGAAAACCCTGCAGGACTACAAGTGCACCAGCG

TGATCCTGGTGCCCACCCTGTTCGCCATCCTGAACAGAAGCGAGCTGCTG

GAAAAGTTCGACCTGAGCAACCTGACCGAGATCGCCTCTGGCGGAGCCCC

TCTGGCCAAAGAAGTGGGAGAAGCCGTCGCCAGACGGTTCAATCTGCCCG

GCGTGCGGCAGGGCTACGGACTGACAGAGACAACCAGCGCCTTCATCATC

ACCCCCGAGGGCGACGATAAGCCTGGCGCCTCTGGAAAGGTGGTGCCCCT

GATGAAGGTCAAAGTGATCGACCTGGACACCAAGAAAACCCTGGGCCCCA

ACAGACGGGGCGAGATCTGTGTGAAGGGCCCCATGCTGATGACCGGCTAC

GAGAAGAACCCCACCGAGACAAAAGAGATCATCGACGAGGACGGCTGGCT

GCACTCTGGCGACATCGGCTACTGGGACGAGGACCACCACTTCTTCATCG

TGGACCGGCTGAAGTCCCTGATCAAGTACAAGGGCTACCAGGTGCCCCCT

GCCGAGCTGGAATCTGTGCTGCTGCAGCATCCCAACATCTTCGATGCCGG

CGTGGCCGGCATCCCTGATCCTGAAGCTGGCGAACTGCCAGGCGCTGTGG

TGGTGCTGGAAAAAGGCAAGCACCTGACAGAGCAGGAAGTGCTGGACTAC

GTCGCCGGCCAGGTGTACAACGCCAAGAGACTGAGAGGCGGCGTGCGCTT

CGTGGATGAAGTGCCTAAGGGCCTGACCGGCAAGATCGACGCCAAGGCCA

TCAGAGAGATCCTGAAGAAACCCCAGGCCAAGATGTGA
```

The amino acid sequence encoded by the optimized base sequence is represented by SEQ ID NO: 5. The amino acid sequence of SEQ ID NO: 5 is the same as the amino acid sequence of SEQ ID NO: 1.

Further, a mutation (S283G), in which serine at the 283rd position from the N-terminal side of the encoded amino acid sequence was substituted by glycine, was introduced to the optimized luciferase gene. In the introduction of the mutation, KroiwaOkisj(m)S283G primer: (GAC TAC AAG TGC ACC GGC GTG ATC CTG GTG CCC: SEQ ID NO: 33) was used.

Thereby, a gene having the base sequence represented by SEQ ID NO: 39 was obtained. The luciferase encoded by the gene is referred to as "mutant 1" or "S283G mutant." The amino acid sequence of the mutant 1 is represented by SEQ ID NO: 38. The mutant 1 showed luminescence which has a brightness higher than that of the wild type luciferase and whose color shifted to a long wavelength side.

The introduction of the mutation was performed base on the descriptions of a literature (Asako Sawano and Atsushi Miyawaki, Nucleic Acids Research, 2000, Vol. 28, No. 16).

Example 3: Random Mutation Introduction

Mutation was randomly introduced into the S283G mutant *Luciora kuroiwae* luciferase, whereby mutant genes expressing the *Luciora kuroiwae* luciferase having further mutation were prepared.

Mutation was randomly introduced into the domain ranging from about 570 bp to about 1132 bp of the luciferase of the mutant 1 (S283G), using GeneMorph II EZClone Domain Mutagenesis Kit (Agilent Inc.). The mutation introduction was performed using a primer set consisting of JP-Kuroiwa(mam)-570-F primer: (cgtggaagtggacaacgagacacac: SEQ ID NO: 36) and JP-Kuroiwa(mam)-1132-R primer: (TGGTGTCCAGGTCGATCACTTTGAC: SEQ ID NO: 37) according to a manual attached to the kit.

The plasmid into which mutation had been introduced was obtained by the method described above, and it was transformed into *E. coli* JM109 (DE3) strains (Promega KK.), thereby forming colonies. D-Luciferin having a final concentration of 2 mM was sprayed to the colonies, and then luminescence was photographed using a CCD camera, DP-70 (Olympus Corporation). Colonies showing orange luminescence brighter than other colonies were picked up, the sequence thereof was read using a sequencer after the introduction of mutation, and it was confirmed that the mutation was randomly introduced into the luciferase gene.

One of the mutation-introduced genes obtained by the method described above is referred to as "mutant 2." A base sequence of the mutant 2 is represented by SEQ ID NO: 41. An amino acid sequence encoded by the base sequence is represented by SEQ ID NO: 40. As shown in SEQ ID NO: 40, the mutant 2 has a mutation (V256A), in which a valine residue at the 256th position from the N-terminal side of the amino acid sequence was substituted by an alanine residue, in addition of the S283G mutation.

Further mutation was randomly introduced into the mutant 2 again. Specifically, mutation was randomly introduced into the same domain as above of the gene of the mutant 2, using GeneMorph II EZClone Domain Mutagenesis Kit (Agilent Inc.).

Colony formation was performed in the same manner as above, and luminescence was photographed. Colonies emitting light at a brightness higher than that of the mutant 2 were obtained, and the luciferase genes thereof were analyzed. One of the genes is referred to as "mutant 3." A base sequence of the mutant 3 is represented by SEQ ID NO: 43. An amino acid sequence encoded by the base sequence was represented by SEQ ID NO: 42. As shown in SEQ ID NO: 42, the mutant 3 has a mutation (R111H), in which a arginine residue at the 111th position from the N-terminal side of the amino acid sequence was substituted by a histidine residue, in addition to the S283G and V256A mutations. The mutation of the residue at the 111th position from the N-terminal side of the amino acid sequence was not intended at the beginning, and thus it is considered that the residue was accidentally substituted in the PCR.

Example 4: Observation of Luminescence and Measurement of Luminescence Intensity and Luminescence Spectrum in HeLa Cell 1. Preparation of Expression Vector Luminescence intensity of the wild type luciferase and the mutant luciferase (the mutants 1 to 3) of *Luciora kuroiwae* obtained in Examples 1 to 3 was measured in a HeLa cell, and the obtained values were compared with that of orange luciferase derived from *Rhagophthalmus ohbai* (SLO luciferase; Toyobo Co., Ltd.).

A Kozak sequence (gccrccatgg: SEQ ID NO: 6) was added to each gene. All of the 4 types of sequences were codon-optimized for the expression in a mammalian cell. After that, the sequence was inserted between SgfI and PmeI sites in a multi-cloning site of pF9A CMV hRLuc neo Flexi vector (Promega KK.). Each gene was inserted into the vector using primers represented by SEQ ID NO: 34 and SEQ ID NO: 35. The pF9A vector contains a *Renilla* luciferase gene (hRLuc) in the vector sequence as an internal control, and thus a luminescence intensity obtained by the luminescent gene inserted into the multi-cloning site can be calculated as a ratio to a luminescence intensity obtained by the *Renilla* luciferase.

According to the same procedures as above, the Kozak sequence was added to the SLO luciferase gene, which was used as a luciferase for comparison, and then it was inserted into the multi-cloning site of the pF9A vector.

2. Luminescence Observation

Each of the 5 types of expression vectors prepared as above was introduced by a lipofection method into the Hela cells seeded in a 48-well plate. At a stage where the gene was expressed, 2 mM of D-luciferin was added thereto as a substrate, and photographing was performed using DP70 color CCD (manufactured by Olympus Corporation) at an exposure time of one minute (ISO 1600). The culture temperature of the cells was adjusted to about 37° C.

Images acquired by the photographing are shown in FIG. 1. In FIG. 1, the results of the mutant 1, mutant 2, mutant 3, wild type and SLO in the 4 wells are shown in order from the top. In FIG. 1, the observation results acquired in color are shown in monochrome.

As shown in FIG. 1, in the wild type *Luciora kuroiwae* luciferase and the SLO luciferase, clear luminescence images could not obtained in the photographing conditions described above. On the other hand, clear luminescence images could be obtained in the mutants 1 to 3. From the results acquired in color, the luminescence in the mutant 1 was reddish light, and the luminescence in the mutants 2 and 3 was orange light.

3. Comparison in Luminescence Intensity

Next, the luminescence intensities were compared. This comparison was performed using Dual-Glo (registered trademark) Luciferase Assay System (manufactured by Promega Corporation, Product No. E2940). Each of the 5 types of expression vectors was introduced by a lipofection method into the Hela cells seeded in a 48-well plate, and the cells were washed with PBS after 22 hours. 200 µl of 2 mM D-luciferin/CO2 Independent Medium (Invitrogen) was added to each well of the 48-well plate, and luminescence intensity was measured for 60 minutes at 37° C. using Luminescensor (ATTO) in a condition of a measurement time of 1 second per well. The luminescence intensity at a point of time when 60 minutes passed was determined as the luminescence intensity of each of the 5 types of luciferases. After that, according to the manual, coelenterazine was added, and the luminescence intensity obtained by the *Renilla* luciferase, which is an internal control, was measured for 15 minutes at 37° C. using the Luminescensor in a condition of measurement time of 1 second per well. The luminescence intensity obtained by each of the *Luciora kuroiwae* wild type luciferase, the mutants 1 to 3, and the SLO luciferase was divided by the luminescence intensity obtained by the *Renilla* luciferase, and the calculated value was determined as the luminescence intensity of each luciferase and graphed.

The results are shown in FIG. 2. As shown in FIG. 2, when the *Luciora kuroiwae* luciferase was expressed in the HeLa cells, the luminescence intensity was 1.2 times higher in the wild type, 17.1 times higher in the mutant 1, 20.6 times higher in the mutant 2, and 29.1 times higher in the mutant 3, than the luminescence intensity obtained by the SLO luciferase. It was found that the orange luminescence obtained in the mutants 2 and 3 had a very high brightness compared to the conventional orange luciferase.

4. Measurement of Luminescence Spectrum

Next, a luminescence spectrum was measured.

LumiFlSpectroCapture (ATTO) (slit width: 0.5 mm, exposure time: one minute) was used as an apparatus for measurement. HeLa cells expressing each luciferase gene were suspended in a solution containing 2 mM D-luciferin/CO2 Independent Medium (Invitrogen) to cause the luminescence in the cells, and a luminescence spectrum was measured in a condition of 37° C. The HeLa cells were treated with trypsin and floated.

The measured luminescence spectra are shown in FIG. 3. In addition, the maximum luminescent wavelengths of the luciferases are shown in Table 1 below. The "maximum luminescent wavelength" means a wavelength in the case where the maximum luminescence intensity is obtained in a spectrum obtained by measuring luminescence of luciferin caused by the luciferase.

TABLE 1

| Name of luciferase | Maximum luminescent wavelength |
|---|---|
| SLO | 594 |
| Wild type of Luciora kuroiwae | 585 |
| Mutant 1 of Luciora kuroiwae (S283G) | 606 |
| Mutant 2 of Luciora kuroiwae (S283G, V256A) | 590 |
| Mutant 3 of Luciora kuroiwae (R111H, S283G, V256A) | 590 |

From FIG. 3 and Table 1, the wild type *Luciora kuroiwae* luciferase showed the maximum luminescent wavelength of about 585 nm in the HeLa cells floating in a medium at about 37° C. In the same conditions, the maximum luminescent wavelength was about 606 nm in the mutant 1, about 590 nm in the mutant 2, about 590 nm in the mutant 3, and about 594 nm in the SLO luciferase (Toyobo Co., Ltd.).

In the mutant 1, the maximum luminescent wavelength shifted to the slightly long wavelength side, whereas almost the same maximum luminescent wavelength as that of the SLO luciferase was shown in the mutants 2 and 3.

From FIG. 3, it was found that each spectrum obtained in the mutants 1 to 3 was one sharp peak.

From the above, it was found that the mutants 2 and 3 of *Luciora kuroiwae* luciferase had a luminescence intensity 20.6 times higher and 29.1 times higher, respectively, than the luminescence intensity obtained by the SLO luciferase, while showing almost the same maximum luminescent wavelength as that of the SLO luciferase.

It can be considered that when the multicolor assay is performed using the mutant 2 or 3, which is an orange luciferase having a higher brightness than ever, as the reporter, it is possible to effectively obtain the signals in the orange region.

What is claimed is:

1. A luciferase comprising an amino acid sequence which has 95% or more homology to the entire length of the amino acid sequence of SEQ ID NO: 40 and which has a glycine residue and an alanine residue at positions corresponding to the 283rd and 256th positions from the N-terminal side of SEQ ID NO: 40, respectively, wherein the amino acid sequence is a luciferase that catalyzes a luminescence reaction that generates luminescence having the maximum luminescent wavelength of 570 nm to 610 nm.

2. A luciferase comprising an amino acid sequence which has 95% or more homology to the entire length of the amino acid sequence of SEQ ID NO: 42 and which has a glycine residue and an alanine residue at positions corresponding to the 283rd and 256th positions from the N-terminal side of SEQ ID NO: 42, respectively,
wherein the amino acid sequence is a luciferase that catalyzes a luminescence reaction that generates luminescence having the maximum luminescent wavelength of 570 nm to 610 nm.

3. The luciferase according to claim 1, wherein the homology to the entire length of the amino acid sequence of SEQ ID NO: 40 is 98% or more.

4. The luciferase according to claim 1, wherein the homology to the entire length of the amino acid sequence of SEQ ID NO: 40 is 99% or more.

5. The luciferase according to claim 1, wherein the luciferase has the amino acid sequence of SEQ ID NO: 40.

6. The luciferase according to claim 2, wherein the homology to the entire length of the amino acid sequence of SEQ ID NO: 42 is 98% or more.

7. The luciferase according to claim 2, wherein the homology to the entire length of the amino acid sequence of SEQ ID NO: 42 is 99% or more.

8. The luciferase according to claim 2, wherein the luciferase has the amino acid sequence of SEQ ID NO: 42.

9. A luciferase comprising an amino acid sequence which has 95% or more homology to the entire length of the amino acid sequence of SEQ ID NO: 38 and which has a glycine residue and an alanine residue at positions corresponding to the 283rd and 256th positions from the N-terminal side of SEQ ID NO: 38, respectively,
wherein the amino acid sequence is a luciferase that catalyzes a luminescence reaction that generates luminescence having the maximum luminescent wavelength of 570 nm to 610 nm.

10. The luciferase according to claim 9, wherein the homology to the entire length of the amino acid sequence of SEQ ID NO: 38 is 96% or more.

11. The luciferase according to claim 9, wherein the homology to the entire length of the amino acid sequence of SEQ ID NO: 38 is 97% or more.

12. The luciferase according to claim 9, wherein the homology to the entire length of the amino acid sequence of SEQ ID NO: 38 is 98% or more.

13. The luciferase according to claim 9, wherein the homology to the entire length of the amino acid sequence of SEQ ID NO: 38 is 99% or more.

14. The luciferase according to claim 9, wherein the homology to the entire length of the amino acid sequence of SEQ ID NO: 38 is 99.5% or more.

15. The luciferase according to claim 9, wherein the homology to the entire length of the amino acid sequence of SEQ ID NO: 38 is 99.8% or more.

16. The luciferase according to claim 9, wherein the luciferase has the amino acid sequence of SEQ ID NO: 38.

* * * * *

SEQUENCE LISTING

<160> NUMBER OF SEQ ID NOS: 49

<210> SEQ ID NO 1
<211> LENGTH: 545

<212> TYPE: PRT
<213> ORGANISM: Luciola kuroiwae

<400> SEQUENCE: 1

```
Met Glu Lys Glu Glu Asn Val Ile Tyr Gly Pro Glu Pro Phe Tyr Pro
1               5                   10                  15

Val Glu Glu Gly Ser Ala Gly Thr Gln Leu His Arg Phe Met Glu Arg
            20                  25                  30

Tyr Ala Lys Met Gly Ala Ile Cys Phe Ser Asn Ala Leu Thr Gly Gln
        35                  40                  45

Asp Val Thr Tyr Ala Glu Tyr Phe Asp Arg Ser Val Arg Leu Ala Glu
    50                  55                  60

Ala Leu Arg Arg His Gly Leu Thr Pro Glu Lys Lys Ile Gly Ile Cys
65                  70                  75                  80

Ser Glu Asn Cys Leu Glu Phe Phe Ile Pro Val Leu Ser Gly Ala Tyr
                85                  90                  95

Ile Ala Ser Pro Val Ala Pro Thr Asn Glu Ile Tyr Thr Ile Arg Glu
            100                 105                 110

Leu Val His Ser Phe Gly Ile Ser Glu Pro Met Ile Val Phe Ser Ser
        115                 120                 125

Lys Lys Gly Leu Asp Lys Val Leu Glu Val Gln Lys Thr Val His Ser
    130                 135                 140

Ile Lys Thr Ile Val Ile Asp Ser Ser Thr Thr Tyr Arg Gly Tyr
145                 150                 155                 160

Asp Ser Met Asp Ala Phe Val Lys Lys Tyr Val Pro Ala Asn Phe Asn
                165                 170                 175

Leu Ser Glu Phe Lys Thr Val Glu Val Asp Asn Glu Thr His Thr Leu
            180                 185                 190

Leu Ile Met Asn Ser Ser Gly Ser Thr Gly Leu Pro Lys Gly Val Leu
        195                 200                 205

Val Arg His Cys Gly Ala Val Thr Arg Phe Ser His Cys Arg Asp Pro
    210                 215                 220

Ile Phe Gly Asn Gln Val Ser Pro Gly Thr Ala Ile Leu Thr Val Val
225                 230                 235                 240

Pro Phe His His Gly Phe Gly Met Phe Thr Thr Leu Gly Tyr Phe Val
                245                 250                 255

Cys Gly Tyr Arg Ile Val Met Leu Thr Lys Phe Asp Asp Glu Val Leu
            260                 265                 270

Leu Lys Thr Leu Gln Asp Tyr Lys Cys Thr Ser Val Ile Leu Val Pro
        275                 280                 285

Thr Leu Phe Ala Ile Leu Asn Arg Ser Glu Leu Leu Glu Lys Phe Asp
    290                 295                 300

Leu Ser Asn Leu Thr Glu Ile Ala Ser Gly Gly Ala Pro Leu Ala Lys
305                 310                 315                 320

Glu Val Gly Glu Ala Val Ala Arg Arg Phe Asn Leu Pro Gly Val Arg
                325                 330                 335

Gln Gly Tyr Gly Leu Thr Glu Thr Thr Ser Ala Phe Ile Ile Thr Pro
            340                 345                 350

Glu Gly Asp Asp Lys Pro Gly Ala Ser Gly Lys Val Val Pro Leu Met
        355                 360                 365

Lys Val Lys Val Ile Asp Leu Asp Thr Lys Lys Thr Leu Gly Pro Asn
    370                 375                 380

Arg Arg Gly Glu Ile Cys Val Lys Gly Pro Met Leu Met Thr Gly Tyr
385                 390                 395                 400
```

```
Glu Lys Asn Pro Thr Glu Thr Lys Glu Ile Ile Asp Glu Asp Gly Trp
                405                 410                 415
Leu His Ser Gly Asp Ile Gly Tyr Trp Asp Glu Asp His His Phe Phe
            420                 425                 430
Ile Val Asp Arg Leu Lys Ser Leu Ile Lys Tyr Lys Gly Tyr Gln Val
        435                 440                 445
Pro Pro Ala Glu Leu Glu Ser Val Leu Leu Gln His Pro Asn Ile Phe
    450                 455                 460
Asp Ala Gly Val Ala Gly Ile Pro Asp Pro Glu Ala Gly Glu Leu Pro
465                 470                 475                 480
Gly Ala Val Val Val Leu Glu Lys Gly Lys His Leu Thr Glu Gln Glu
                485                 490                 495
Val Leu Asp Tyr Val Ala Gly Gln Val Tyr Asn Ala Lys Arg Leu Arg
            500                 505                 510
Gly Gly Val Arg Phe Val Asp Glu Val Pro Lys Gly Leu Thr Gly Lys
        515                 520                 525
Ile Asp Ala Lys Ala Ile Arg Glu Ile Leu Lys Lys Pro Gln Ala Lys
    530                 535                 540
Met
545

<210> SEQ ID NO 2
<211> LENGTH: 1638
<212> TYPE: DNA
<213> ORGANISM: Luciola kuroiwae

<400> SEQUENCE: 2
atggaaaaag aagaaaatgt gatatacggt cccgagccgt tttacccgt cgaagaggga     60 tctgcaggaa cgcaactgca cagatttatg gagcgatacg ccaaaatggg ggctatatgt    120
ttttctaacg ccctcacggg ccaagatgta acgtatgccg aatattttga ccgatcggtt    180
cgtttagcgg aagctttgag aaggcacggc ttaacgccag agaaaaaaat cggtatttgc    240
agcgaaaatt gcttagaatt tttcattccg gtgctttcgg gagcgtatat cgcttcaccc    300
gtcgctccaa ctaacgaaat ttacactata cgcgaattgg ttcacagttt tggaatatcc    360
gagccaatga tcgtgtttag ctcaaagaaa ggattggata agtcttgga agtacaaaaa    420 acagtgcact ctattaaaac aatagtcatt attgatagct caactactta tcgaggatat    480
gacagcatgg atgcgtttgt taaaaatac gtacccgcaa atttcaattt atccgaattc    540
aaaactgtag aagtcgataa tgaaactcac actcttctta atgaactc gtccggttcc    600 accggtctac cgaaaggtgt gctagtccgt cattgtgggg cagttacaag atttttctcat    660 tgcagggatc cgattttttgg taatcaagtt tcaccaggca cagcaatttt aacggtcgtt    720
ccgttccatc atggctttgg tatgttcact actttaggat actttgtttg tggataccga    780
atcgtaatgt taacaaaatt tgatgacgaa gtattgttga aaaccctaca agattataag    840
tgtactagtg ttatcctagt accaactttg ttcgctatcc ttaatagaag tgaactactg    900
gagaaattcg acttgtctaa tctgactgaa attgcatctg gtggtgcccc attagcaaaa    960
gaagttgggg aagccgttgc cagaagattt aatcttcctg gtgttcgcca aggttacggt   1020
ttaactgaaa ccacatccgc ttttattatc accccagaag gggatgacaa accaggggct   1080
tctggaaaag ttgtgccttt aatgaaagtt aaagtgattg atcttgacac taagaaaacg   1140
cttggtccta accgtcgtgg agaaatttgc gttaagggtc ctatgttgat gacaggttac   1200
```

```
gagaagaatc ctacagaaac taaagaaatt atcgacgaag atggttggct gcacagtgga    1260
gatattgggt attgggacga agatcatcac ttctttattg tagatcgtct caaatcctta    1320
atcaaataca aaggatatca agtaccacct gctgaattgg aatccgtact tttacaacat    1380
ccaaatatat ttgatgccgg tgttgccgga attcccgatc cgaagccgg ggagcttccg     1440 ggtgctgtgg ttgtattaga gaaggaaaa catctaactg aacaagaagt attggattac     1500
gttgccggac aagtttacaa cgcaaaacgt ttacgcggtg cgttcgtttt tgtagacgag    1560
gtacctaaag gtctcactgg aaaaattgac gcaaaggcaa ttagagaaat tcttaagaag    1620
ccgcaagcta agatgtga                                                  1638

<210> SEQ ID NO 3
<211> LENGTH: 1638
<212> TYPE: DNA
<213> ORGANISM: Luciola kuroiwae

<400> SEQUENCE: 3
atggaaaaag aagaaaatgt gatatacggt cccgagccgt tttaccccgt cgaagaggga    60
tctgcaggaa cgcaactgca cagatttatg gagcgatacg ccaaaatggg ggctatatgt    120
ttttctaacg ccctcacggg ccaagatgta acgtatgccg aatatttga ccgatcggtt     180 cgtttagcgg aagctttgag aaggcacggc ttaacgccag agaaaaaaat cggtatttgc    240
agcgaaaatt gcttagaatt tttcattccg gtgcttccgg gagcgtatat cgcttcaccc    300
gtcgctccaa ctaacgaaat ttacactata cgcgaattgg ttcacagttt tggaatatcc    360
gagccaatga tcgtgtttag ctcaagaaaa ggattggata agtcttgga agtacaaaaa     420 acagtgcact ctattaaaac aatagtcatt attgatagct caactactta tcgaggatat    480
gacagcatga tgcgtttgt taaaaaatac gtacccgcaa atttcaattt atccgaattt     540
aaaactgtag aagtcgataa tgaaactcac actcttctta aatgaactc gtccggttcc     600 accggtctac cgaaaggtgt gctagtccgt cattgtgggg cagttacaag attttctcat    660
tgcagagatc cgattttttgg taatcaagtt tcaccaggca cagcaatttt aacggtcgtt    720
ccgttccatc atggctttgg tatgttcact actttaggat actttgtttg tggataccga    780
atcgtaatgt taacaaaatt tgatgacgaa gtattgttga aaaccctaca agattataag    840
tgtactagtg ttatcctagt accaactttg ttcgctatcc ttaatagaag tgaactactg    900
gagaaattcg acttgtctaa tctgactgaa attgcatctg gtggtgcccc attagcaaaa    960
gaagttgggg aagccgttgc cagaagattt aatcttcctg gtgttcgcca aggttacggt    1020
ttaactgaaa ccacatccgc tttatattatc accccagaag gggatgacaa accaggggct   1080 tctgaaaag ttgtgccttt aatgaaagtt aaagtgattg atcttgacac taagaaaacg    1140
cttggtccta accgtcgtgg agaaatttgc gttaagggtc ctatgttgat gacaggttac    1200
gagaagaatc ctacagaaac taaagaaatt atcgacgaag atggttggct gcacagtgga    1260
gatattgggt attgggacga agatcatcac ttctttattg tagatcgtct caaatcctta    1320
atcaaataca aggatatca agtaccacct gctgaattgg aatccgtact tttacaacat     1380
ccaaatatat ttgatgccgg tgttgccggt attcccgatc cgaagccgg ggagcttccg     1440 ggtgctgtgg ttgtattaga gaaggaaaa catctaactg aacaagaagt attggattac     1500
gttgccggac aagtttacaa cgcaaaacgt ttacgcggtg cgttcgtttt tgtagacgag    1560
gtacctaaag gtctcactgg aaaaattgac gcaaaggcaa ttagagaaat tcttaagaag    1620
ccgcaagcta agatgtga                                                  1638
```

<210> SEQ ID NO 4
<211> LENGTH: 1638
<212> TYPE: DNA
<213> ORGANISM: Luciola kuroiwae

<400> SEQUENCE: 4

```
atggaaaaag aggaaaacgt catctacggc cccgagccct tctaccctgt ggaagaaggc      60
agcgccggca cccagctgca ccggttcatg gaaagatacg ccaagatggg cgccatctgc     120
ttcagcaatg ccctgaccgg ccaggacgtg acctacgccg agtacttcga cagaagcgtg     180
cggctggccg aggccctgag aaggcatgga ctgacccccg agaagaagat cggcatctgc     240
agcgagaact gcctggaatt tttcatcccc gtgctgagcg gcgcctatat cgcctctcct     300
gtggccccca ccaacgagat ctacaccatc cgcgagctgg tgcacagctt cggcatcagc     360
gagcccatga tcgtgttcag cagcaagaaa ggcctggaca aggtgctgga agtgcagaaa     420
accgtgcaca gcatcaagac catcgtgatc atcgacagca gcaccaccta ccggggctac     480
gacagcatgg acgccttcgt gaagaaatac gtgcccgcca acttcaacct gagcgagttc     540
aagaccgtgg aagtggacaa cgagacacac accctgctga tcatgaacag ctccggcagc     600
accggcctgc ctaaaggcgt gctcgtcaga cattgtggcg ccgtgacccg gttcagccac     660
tgcagagatc ccatcttcgg aaaccaggtg tcccccggca ccgccattct gaccgtggtg     720
cctttccacc acggcttcgg catgttcacc accctgggct acttcgtgtg cggctaccgg     780
atcgtgatgc tgaccaagtt cgacgacgag gtgctgctga aaaccctgca ggactacaag     840
tgcaccagcg tgatcctggt gcccacccty ttcgccatcc tgaacagaag cgagctgctg     900
gaaaagttcg acctgagcaa cctgaccgag atcgcctctg cggagccccc tctggccaaa     960
gaagtgggag aagccgtcgc cagacggttc aatctgcccg cgtgcggca gggctacgga    1020
ctgacagaga caaccagcgc cttcatcatc ccccccgagg cgacgataa gcctggcgcc    1080
tctggaaagg tggtgccccct gatgaaggtc aaagtgatcg acctggacac caagaaaacc    1140
ctgggcccca cagacggggg cgagatctgt gtgaagggcc ccatgctgat gaccggctac    1200
gagaagaacc ccaccgagac aaaagagatc atcgacgagg acggctggct gcactctggc    1260
gacatcggct actgggacga ggaccaccac ttcttcatcg tggaccggct gaagtccctg    1320
atcaagtaca agggctacca ggtgccccct gccgagctgg aatctgtgct gctgcagcat    1380
cccaacatct tcgatgccgg cgtggccggc atccctgatc ctgaagctgg cgaactgcca    1440
ggcgctgtgg tggtgctgga aaaaggcaag cacctgacag agcaggaagt gctggactac    1500
gtcgccggcc aggtgtacaa cgccaagaga ctgagaggcg gcgtgcgctt cgtggatgaa    1560
gtgcctaagg gcctgaccgg caagatcgac gccaaggcca tcagagagat cctgaagaaa    1620
ccccaggcca agatgtga                                                 1638
```

<210> SEQ ID NO 5
<211> LENGTH: 545
<212> TYPE: PRT
<213> ORGANISM: Luciola kuroiwae

<400> SEQUENCE: 5

Met Glu Lys Glu Glu Asn Val Ile Tyr Gly Pro Glu Pro Phe Tyr Pro
1               5                   10                  15

Val Glu Glu Gly Ser Ala Gly Thr Gln Leu His Arg Phe Met Glu Arg
            20                  25                  30

```
Tyr Ala Lys Met Gly Ala Ile Cys Phe Ser Asn Ala Leu Thr Gly Gln
         35                  40                  45

Asp Val Thr Tyr Ala Glu Tyr Phe Asp Arg Ser Val Arg Leu Ala Glu
 50                  55                  60

Ala Leu Arg Arg His Gly Leu Thr Pro Glu Lys Lys Ile Gly Ile Cys
 65                  70                  75                  80

Ser Glu Asn Cys Leu Glu Phe Phe Ile Pro Val Leu Ser Gly Ala Tyr
                 85                  90                  95

Ile Ala Ser Pro Val Ala Pro Thr Asn Glu Ile Tyr Thr Ile Arg Glu
             100                 105                 110

Leu Val His Ser Phe Gly Ile Ser Glu Pro Met Ile Val Phe Ser Ser
         115                 120                 125

Lys Lys Gly Leu Asp Lys Val Leu Glu Val Gln Lys Thr Val His Ser
 130                 135                 140

Ile Lys Thr Ile Val Ile Asp Ser Ser Thr Thr Tyr Arg Gly Tyr
 145                 150                 155                 160

Asp Ser Met Asp Ala Phe Val Lys Lys Tyr Val Pro Ala Asn Phe Asn
             165                 170                 175

Leu Ser Glu Phe Lys Thr Val Glu Val Asp Asn Glu Thr His Thr Leu
         180                 185                 190

Leu Ile Met Asn Ser Ser Gly Ser Thr Gly Leu Pro Lys Gly Val Leu
 195                 200                 205

Val Arg His Cys Gly Ala Val Thr Arg Phe Ser His Cys Arg Asp Pro
     210                 215                 220

Ile Phe Gly Asn Gln Val Ser Pro Gly Thr Ala Ile Leu Thr Val Val
225                 230                 235                 240

Pro Phe His His Gly Phe Gly Met Phe Thr Thr Leu Gly Tyr Phe Val
             245                 250                 255

Cys Gly Tyr Arg Ile Val Met Leu Thr Lys Phe Asp Asp Glu Val Leu
         260                 265                 270

Leu Lys Thr Leu Gln Asp Tyr Lys Cys Thr Ser Val Ile Leu Val Pro
     275                 280                 285

Thr Leu Phe Ala Ile Leu Asn Arg Ser Glu Leu Leu Glu Lys Phe Asp
 290                 295                 300

Leu Ser Asn Leu Thr Glu Ile Ala Ser Gly Gly Ala Pro Leu Ala Lys
305                 310                 315                 320

Glu Val Gly Glu Ala Val Ala Arg Arg Phe Asn Leu Pro Gly Val Arg
             325                 330                 335

Gln Gly Tyr Gly Leu Thr Glu Thr Thr Ser Ala Phe Ile Ile Thr Pro
         340                 345                 350

Glu Gly Asp Asp Lys Pro Gly Ala Ser Gly Lys Val Val Pro Leu Met
     355                 360                 365

Lys Val Lys Val Ile Asp Leu Asp Thr Lys Lys Thr Leu Gly Pro Asn
 370                 375                 380

Arg Arg Gly Glu Ile Cys Val Lys Gly Pro Met Leu Met Thr Gly Tyr
385                 390                 395                 400

Glu Lys Asn Pro Thr Glu Thr Lys Glu Ile Ile Asp Glu Asp Gly Trp
             405                 410                 415

Leu His Ser Gly Asp Ile Gly Tyr Trp Asp Glu Asp His His Phe Phe
         420                 425                 430

Ile Val Asp Arg Leu Lys Ser Leu Ile Lys Tyr Lys Gly Tyr Gln Val
     435                 440                 445

Pro Pro Ala Glu Leu Glu Ser Val Leu Leu Gln His Pro Asn Ile Phe
```

```
                    450             455             460
Asp Ala Gly Val Ala Gly Ile Pro Asp Pro Glu Ala Gly Glu Leu Pro
465                 470                 475                 480

Gly Ala Val Val Leu Glu Lys Gly Lys His Leu Thr Glu Gln Glu
                485                 490                 495

Val Leu Asp Tyr Val Ala Gly Gln Val Tyr Asn Ala Lys Arg Leu Arg
            500                 505                 510

Gly Gly Val Arg Phe Val Asp Glu Val Pro Lys Gly Leu Thr Gly Lys
                515                 520                 525

Ile Asp Ala Lys Ala Ile Arg Glu Ile Leu Lys Pro Gln Ala Lys
            530                 535                 540

Met
545

<210> SEQ ID NO 6
<211> LENGTH: 10
<212> TYPE: DNA
<213> ORGANISM: Artificial
<220> FEATURE:
<223> OTHER INFORMATION: Kozak sequence

<400> SEQUENCE: 6 gccrccatgg                                                          10

<210> SEQ ID NO 7
<211> LENGTH: 9
<212> TYPE: PRT
<213> ORGANISM: Artificial
<220> FEATURE:
<223> OTHER INFORMATION: consensus sequence in luciferases

<400> SEQUENCE: 7

Leu Ile Lys Tyr Lys Gly Tyr Gln Val
1               5

<210> SEQ ID NO 8
<211> LENGTH: 23
<212> TYPE: DNA
<213> ORGANISM: Artificial
<220> FEATURE:
<223> OTHER INFORMATION: flexLuc5-ATA
<220> FEATURE:
<221> NAME/KEY: misc_feature
<222> LOCATION: (9)..(9)
<223> OTHER INFORMATION: n is a, c, g, or t

<400> SEQUENCE: 8
acytgrtanc cyttatattt aat                                           23

<210> SEQ ID NO 9
<211> LENGTH: 23
<212> TYPE: DNA
<213> ORGANISM: Artificial
<220> FEATURE:
<223> OTHER INFORMATION: flexLuc5-ATG
<220> FEATURE:
<221> NAME/KEY: misc_feature
<222> LOCATION: (9)..(9)
<223> OTHER INFORMATION: n is a, c, g, or t

<400> SEQUENCE: 9
acytgrtanc cyttatattt gat                                           23

<210> SEQ ID NO 10
```

```
<211> LENGTH: 23
<212> TYPE: DNA
<213> ORGANISM: Artificial
<220> FEATURE:
<223> OTHER INFORMATION: flexLuc5-ATT
<220> FEATURE:
<221> NAME/KEY: misc_feature
<222> LOCATION: (9)..(9)
<223> OTHER INFORMATION: n is a, c, g, or t

<400> SEQUENCE: 10
acytgrtanc cyttatattt tat                                           23

<210> SEQ ID NO 11
<211> LENGTH: 23
<212> TYPE: DNA
<213> ORGANISM: Artificial
<220> FEATURE:
<223> OTHER INFORMATION: flexLuc5-ACA
<220> FEATURE:
<221> NAME/KEY: misc_feature
<222> LOCATION: (9)..(9)
<223> OTHER INFORMATION: n is a, c, g, or t

<400> SEQUENCE: 11
acytgrtanc cyttatactt aat                                           23

<210> SEQ ID NO 12
<211> LENGTH: 23
<212> TYPE: DNA
<213> ORGANISM: Artificial
<220> FEATURE:
<223> OTHER INFORMATION: flexLuc5-ACG
<220> FEATURE:
<221> NAME/KEY: misc_feature
<222> LOCATION: (9)..(9)
<223> OTHER INFORMATION: n is a, c, g, or t

<400> SEQUENCE: 12
acytgrtanc cyttatactt gat                                           23

<210> SEQ ID NO 13
<211> LENGTH: 23
<212> TYPE: DNA
<213> ORGANISM: Artificial
<220> FEATURE:
<223> OTHER INFORMATION: flexLuc5-ACT
<220> FEATURE:
<221> NAME/KEY: misc_feature
<222> LOCATION: (9)..(9)
<223> OTHER INFORMATION: n is a, c, g, or t

<400> SEQUENCE: 13
acytgrtanc cyttatactt tat                                           23

<210> SEQ ID NO 14
<211> LENGTH: 23
<212> TYPE: DNA
<213> ORGANISM: Artificial
<220> FEATURE:
<223> OTHER INFORMATION: flexLuc5-GTA
<220> FEATURE:
<221> NAME/KEY: misc_feature
<222> LOCATION: (9)..(9)
<223> OTHER INFORMATION: n is a, c, g, or t

<400> SEQUENCE: 14
acytgrtanc cyttgtattt aat                                           23
```

```
<210> SEQ ID NO 15
<211> LENGTH: 23
<212> TYPE: DNA
<213> ORGANISM: Artificial
<220> FEATURE:
<223> OTHER INFORMATION: flexLuc5-GTG
<220> FEATURE:
<221> NAME/KEY: misc_feature
<222> LOCATION: (9)..(9)
<223> OTHER INFORMATION: n is a, c, g, or t

<400> SEQUENCE: 15
acytgrtanc cyttgtattt gat                                              23

<210> SEQ ID NO 16
<211> LENGTH: 23
<212> TYPE: DNA
<213> ORGANISM: Artificial
<220> FEATURE:
<223> OTHER INFORMATION: flexLuc5-GTT
<220> FEATURE:
<221> NAME/KEY: misc_feature
<222> LOCATION: (9)..(9)
<223> OTHER INFORMATION: n is a, c, g, or t

<400> SEQUENCE: 16
acytgrtanc cyttgtattt tat                                              23

<210> SEQ ID NO 17
<211> LENGTH: 23
<212> TYPE: DNA
<213> ORGANISM: Artificial
<220> FEATURE:
<223> OTHER INFORMATION: flexLuc5-GCA
<220> FEATURE:
<221> NAME/KEY: misc_feature
<222> LOCATION: (9)..(9)
<223> OTHER INFORMATION: n is a, c, g, or t

<400> SEQUENCE: 17
acytgrtanc cyttgtactt aat                                              23

<210> SEQ ID NO 18
<211> LENGTH: 23
<212> TYPE: DNA
<213> ORGANISM: Artificial
<220> FEATURE:
<223> OTHER INFORMATION: flexLuc5-GCG
<220> FEATURE:
<221> NAME/KEY: misc_feature
<222> LOCATION: (9)..(9)
<223> OTHER INFORMATION: n is a, c, g, or t

<400> SEQUENCE: 18
acytgrtanc cyttgtactt gat                                              23

<210> SEQ ID NO 19
<211> LENGTH: 23
<212> TYPE: DNA
<213> ORGANISM: Artificial
<220> FEATURE:
<223> OTHER INFORMATION: flexLuc5-GCT
<220> FEATURE:
<221> NAME/KEY: misc_feature
<222> LOCATION: (9)..(9)
<223> OTHER INFORMATION: n is a, c, g, or t

<400> SEQUENCE: 19
acytgrtanc cyttgtactt tat                                              23
```

```
<210> SEQ ID NO 20
<211> LENGTH: 23
<212> TYPE: DNA
<213> ORGANISM: Artificial
<220> FEATURE:
<223> OTHER INFORMATION: GeneRacer5' Primer

<400> SEQUENCE: 20
cgactggagc acgaggacac tga                                          23

<210> SEQ ID NO 21
<211> LENGTH: 26
<212> TYPE: DNA
<213> ORGANISM: Artificial
<220> FEATURE:
<223> OTHER INFORMATION: GeneRacer5' Nested Primer

<400> SEQUENCE: 21
ggacactgac atggactgaa ggagta                                       26

<210> SEQ ID NO 22
<211> LENGTH: 19
<212> TYPE: DNA
<213> ORGANISM: Artificial
<220> FEATURE:
<223> OTHER INFORMATION: M13-F(-29) Primer

<400> SEQUENCE: 22
cacgacgttg taaaacgac                                               19

<210> SEQ ID NO 23
<211> LENGTH: 18
<212> TYPE: DNA
<213> ORGANISM: Artificial
<220> FEATURE:
<223> OTHER INFORMATION: M13 Reverse

<400> SEQUENCE: 23
ggataacaat ttcacagg                                                18

<210> SEQ ID NO 24
<211> LENGTH: 653
<212> TYPE: DNA
<213> ORGANISM: Luciola kuroiwae

<400> SEQUENCE: 24
gttcggtata ctcgcgagtt cgggcaaaaa ataacaagta gcgcaagatg gaaaaagaag    60
aaaatgtgat atacggtccc gagccgtttt accccgtcga gagggatct gcaggaacgc    120 aactgcacag atttatggag cgatacgcca aatgggggc tatatgtttt tctaacgccc    180
tcacgggcca agatgtaacg tatgccgaat attttgaccg accggttcgt ttagcggaag    240
ctttgagaag gcacggctta acgccagaga aaaaaatcgg tatttgcagc gaaaattgct    300
tagaattttt cattccggtg ctttcgggag cgtatatcgc ttcacccgtc gctccaacta    360
acgaaattta cactatacgc gaattggttc acagttttgg aatatccgag ccaatgatcg    420
tgtttagctc aaagaaagga ttggataaag tcttggaagt acaaaaaaca gtgcactcta    480
ttaaaacaat agtcattatt gatagctcaa ctacttatcg aggatatgac agcatggatg    540
cgtttgttaa aaaatacgt acccgcaaat ttcaatttat ccgaattcaa aactgtagaa    600
gtcgataatg aaactcacac tcttcttata atgaactcgt ccggttccac cgg          653
```

```
<210> SEQ ID NO 25
<211> LENGTH: 22
<212> TYPE: DNA
<213> ORGANISM: Artificial
<220> FEATURE:
<223> OTHER INFORMATION: No2-Kuroiwa-F1

<400> SEQUENCE: 25
gttcggtata ctcgcgagtt cg                                            22

<210> SEQ ID NO 26
<211> LENGTH: 27
<212> TYPE: DNA
<213> ORGANISM: Artificial
<220> FEATURE:
<223> OTHER INFORMATION: No2-Kuroiwa-F2

<400> SEQUENCE: 26
gttcggtata ctcgcgagtt cgggcaa                                       27

<210> SEQ ID NO 27
<211> LENGTH: 25
<212> TYPE: DNA
<213> ORGANISM: Artificial
<220> FEATURE:
<223> OTHER INFORMATION: GeneRacer3' Primer

<400> SEQUENCE: 27
gctgtcaacg atacgctacg taacg                                         25

<210> SEQ ID NO 28
<211> LENGTH: 23
<212> TYPE: DNA
<213> ORGANISM: Artificial
<220> FEATURE:
<223> OTHER INFORMATION: GeneRacer3' Nested Primer

<400> SEQUENCE: 28
cgctacgtaa cggcatgaca gtg                                           23

<210> SEQ ID NO 29
<211> LENGTH: 39
<212> TYPE: DNA
<213> ORGANISM: Artificial
<220> FEATURE:
<223> OTHER INFORMATION: Kuroiwa-BamHI-F

<400> SEQUENCE: 29
cgcggatccg atggaaaaag aagaaaatgt gatatacgg                          39

<210> SEQ ID NO 30
<211> LENGTH: 37
<212> TYPE: DNA
<213> ORGANISM: Artificial
<220> FEATURE:
<223> OTHER INFORMATION: Kuroiwa-stop-EcoRI-R

<400> SEQUENCE: 30
cgcggaattc tcacatctta gcttgcggct tcttaag                            37

<210> SEQ ID NO 31
<211> LENGTH: 20
<212> TYPE: DNA
<213> ORGANISM: Artificial
<220> FEATURE:
<223> OTHER INFORMATION: T7 promoter Primer
```

```
<400> SEQUENCE: 31
taatacgact cactataggg                                               20

<210> SEQ ID NO 32
<211> LENGTH: 21
<212> TYPE: DNA
<213> ORGANISM: Artificial
<220> FEATURE:
<223> OTHER INFORMATION: T7 Reverse Primer

<400> SEQUENCE: 32
ctagttattg ctcagcggtg g                                             21

<210> SEQ ID NO 33
<211> LENGTH: 33
<212> TYPE: DNA
<213> ORGANISM: Artificial
<220> FEATURE:
<223> OTHER INFORMATION: KroiwaOkisj(m)S283G

<400> SEQUENCE: 33
gactacaagt gcaccggcgt gatcctggtg ccc                                33

<210> SEQ ID NO 34
<211> LENGTH: 38
<212> TYPE: DNA
<213> ORGANISM: Artificial
<220> FEATURE:
<223> OTHER INFORMATION: JP-Kuroiwa-(mam)-Koz-pF9A-SgfI-F

<400> SEQUENCE: 34
gccggcgatc gccatggaaa aagaggaaaa cgtcatct                           38

<210> SEQ ID NO 35
<211> LENGTH: 37
<212> TYPE: DNA
<213> ORGANISM: Artificial
<220> FEATURE:
<223> OTHER INFORMATION: JPKuroiwa(m)pF9A*PmeI-R

<400> SEQUENCE: 35
gccggtttaa actcacatct tggcctgggg tttcttc                            37

<210> SEQ ID NO 36
<211> LENGTH: 25
<212> TYPE: DNA
<213> ORGANISM: Artificial
<220> FEATURE:
<223> OTHER INFORMATION: JP-Kuroiwa(mam)-570-F

<400> SEQUENCE: 36
cgtggaagtg gacaacgaga cacac                                         25

<210> SEQ ID NO 37
<211> LENGTH: 25
<212> TYPE: DNA
<213> ORGANISM: Artificial
<220> FEATURE:
<223> OTHER INFORMATION: JP-Kuroiwa(mam)-1132-R

<400> SEQUENCE: 37
tggtgtccag gtcgatcact ttgac                                         25

<210> SEQ ID NO 38
<211> LENGTH: 545
```

<212> TYPE: PRT
<213> ORGANISM: Luciola kuroiwae

<400> SEQUENCE: 38

```
Met Glu Lys Glu Glu Asn Val Ile Tyr Gly Pro Glu Pro Phe Tyr Pro
1               5                   10                  15
Val Glu Glu Gly Ser Ala Gly Thr Gln Leu His Arg Phe Met Glu Arg
            20                  25                  30
Tyr Ala Lys Met Gly Ala Ile Cys Phe Ser Asn Ala Leu Thr Gly Gln
        35                  40                  45
Asp Val Thr Tyr Ala Glu Tyr Phe Asp Arg Ser Val Arg Leu Ala Glu
    50                  55                  60
Ala Leu Arg Arg His Gly Leu Thr Pro Glu Lys Lys Ile Gly Ile Cys
65                  70                  75                  80
Ser Glu Asn Cys Leu Glu Phe Phe Ile Pro Val Leu Ser Gly Ala Tyr
                85                  90                  95
Ile Ala Ser Pro Val Ala Pro Thr Asn Glu Ile Tyr Thr Ile Arg Glu
            100                 105                 110
Leu Val His Ser Phe Gly Ile Ser Glu Pro Met Ile Val Phe Ser Ser
        115                 120                 125
Lys Lys Gly Leu Asp Lys Val Leu Glu Val Gln Lys Thr Val His Ser
    130                 135                 140
Ile Lys Thr Ile Val Ile Asp Ser Ser Thr Thr Tyr Arg Gly Tyr
145                 150                 155                 160
Asp Ser Met Asp Ala Phe Val Lys Lys Tyr Val Pro Ala Asn Phe Asn
                165                 170                 175
Leu Ser Glu Phe Lys Thr Val Glu Val Asp Asn Glu Thr His Thr Leu
            180                 185                 190
Leu Ile Met Asn Ser Ser Gly Ser Thr Gly Leu Pro Lys Gly Val Leu
        195                 200                 205
Val Arg His Cys Gly Ala Val Thr Arg Phe Ser His Cys Arg Asp Pro
    210                 215                 220
Ile Phe Gly Asn Gln Val Ser Pro Gly Thr Ala Ile Leu Thr Val Val
225                 230                 235                 240
Pro Phe His His Gly Phe Gly Met Phe Thr Thr Leu Gly Tyr Phe Val
                245                 250                 255
Cys Gly Tyr Arg Ile Val Met Leu Thr Lys Phe Asp Asp Glu Val Leu
            260                 265                 270
Leu Lys Thr Leu Gln Asp Tyr Lys Cys Thr Gly Val Ile Leu Val Pro
        275                 280                 285
Thr Leu Phe Ala Ile Leu Asn Arg Ser Glu Leu Leu Glu Lys Phe Asp
    290                 295                 300
Leu Ser Asn Leu Thr Glu Ile Ala Ser Gly Gly Ala Pro Leu Ala Lys
305                 310                 315                 320
Glu Val Gly Glu Ala Val Ala Arg Arg Phe Asn Leu Pro Gly Val Arg
                325                 330                 335
Gln Gly Tyr Gly Leu Thr Glu Thr Thr Ser Ala Phe Ile Ile Thr Pro
            340                 345                 350
Glu Gly Asp Asp Lys Pro Gly Ala Ser Gly Lys Val Val Pro Leu Met
        355                 360                 365
Lys Val Lys Val Ile Asp Leu Asp Thr Lys Lys Thr Leu Gly Pro Asn
    370                 375                 380
Arg Arg Gly Glu Ile Cys Val Lys Gly Pro Met Leu Met Thr Gly Tyr
385                 390                 395                 400
```

```
Glu Lys Asn Pro Thr Glu Thr Lys Glu Ile Ile Asp Glu Asp Gly Trp
            405                 410                 415
Leu His Ser Gly Asp Ile Gly Tyr Trp Asp Glu Asp His His Phe Phe
        420                 425                 430
Ile Val Asp Arg Leu Lys Ser Leu Ile Lys Tyr Lys Gly Tyr Gln Val
            435                 440                 445
Pro Pro Ala Glu Leu Glu Ser Val Leu Leu Gln His Pro Asn Ile Phe
        450                 455                 460
Asp Ala Gly Val Ala Gly Ile Pro Asp Pro Glu Ala Gly Glu Leu Pro
465                 470                 475                 480
Gly Ala Val Val Val Leu Glu Lys Gly Lys His Leu Thr Glu Gln Glu
                485                 490                 495
Val Leu Asp Tyr Val Ala Gly Gln Val Tyr Asn Ala Lys Arg Leu Arg
            500                 505                 510
Gly Gly Val Arg Phe Val Asp Glu Val Pro Lys Gly Leu Thr Gly Lys
        515                 520                 525
Ile Asp Ala Lys Ala Ile Arg Glu Ile Leu Lys Lys Pro Gln Ala Lys
    530                 535                 540
Met
545

<210> SEQ ID NO 39
<211> LENGTH: 1638
<212> TYPE: DNA
<213> ORGANISM: Luciola kuroiwae

<400> SEQUENCE: 39
atggaaaaag aggaaaacgt catctacggc cccgagccct tctaccctgt ggaagaaggc      60
agcgccggca cccagctgca ccggttcatg gaaagatacg ccaagatggg cgccatctgc     120
ttcagcaatg ccctgaccgg ccaggacgtg acctacgccg agtacttcga cagaagcgtg     180
cggctggccg aggccctgag aaggcatgga ctgacccccg agaagaagat cggcatctgc     240
agcgagaact gcctggaatt tttcatcccc gtgctgagcg gcgcctatat cgcctctcct     300 gtggcccca ccaacgagat ctacaccatc cgcgagctgg tgcacagctt cggcatcagc     360
gagcccatga tcgtgttcag cagcaagaaa ggcctggaca aggtgctgga agtgcagaaa     420
accgtgcaca gcatcaagac catcgtgatc atcgacagca gcaccaccta ccggggctac     480
gacagcatgg acgccttcgt gaagaaatac gtgcccgcca acttcaacct gagcgagttc     540
aagaccgtgg aagtggacaa cgagacacac accctgctga tcatgaacag ctccggcagc     600
accggcctgc taaaggcgt gctcgtcaga cattgtggcg ccgtgacccg gttcagccac     660
tgcagagatc ccatcttcgg aaaccaggtg tccccggca ccgccattct gaccgtggtg     720 ccttccacc acggcttcgg catgttcacc accctgggct acttcgtgtg cggctaccgg     780
atcgtgatgc tgaccaagtt cgacgacgag gtgctgctga aaaccctgca ggactacaag     840
tgcaccggcg tgatcctggt gcccacccctg ttcgccatcc tgaacagaag cgagctgctg     900
gaaaagttcg acctgagcaa cctgaccgag atcgcctctg cggagcccc tctggccaaa     960 gaagtgggag aagccgtcgc cagacggttc aatctgcccg cgtgcggca gggctacgga    1020 ctgacagaga caaccagcgc cttcatcatc acccccgagg gcgacgataa gcctggcgcc    1080
tctggaaagg tggtgcccct gatgaaggtc aaagtgatcg acctggacac caagaaaacc    1140
ctgggcccca acagacgggg cgagatctgt gtgaagggcc ccatgctgat gaccggctac    1200
```

-continued

```
gagaagaacc ccaccgagac aaaagagatc atcgacgagg acggctggct gcactctggc   1260
gacatcggct actgggacga ggaccaccac ttcttcatcg tggaccggct gaagtccctg   1320
atcaagtaca agggctacca ggtgccccct gccgagctgg aatctgtgct gctgcagcat   1380
cccaacatct tcgatgccgg cgtggccggc atccctgatc ctgaagctgg cgaactgcca   1440
ggcgctgtgg tggtgctgga aaaaggcaag cacctgacag agcaggaagt gctggactac   1500
gtcgccggcc aggtgtacaa cgccaagaga ctgagaggcg gcgtgcgctt cgtggatgaa   1560
gtgcctaagg gcctgaccgg caagatcgac gccaaggcca tcagagagat cctgaagaaa   1620
ccccaggcca agatgtga                                                 1638

<210> SEQ ID NO 40
<211> LENGTH: 545
<212> TYPE: PRT
<213> ORGANISM: Luciola kuroiwae

<400> SEQUENCE: 40

Met Glu Lys Glu Glu Asn Val Ile Tyr Gly Pro Glu Pro Phe Tyr Pro
1               5                   10                  15

Val Glu Glu Gly Ser Ala Gly Thr Gln Leu His Arg Phe Met Glu Arg
            20                  25                  30

Tyr Ala Lys Met Gly Ala Ile Cys Phe Ser Asn Ala Leu Thr Gly Gln
        35                  40                  45

Asp Val Thr Tyr Ala Glu Tyr Phe Asp Arg Ser Val Arg Leu Ala Glu
    50                  55                  60

Ala Leu Arg Arg His Gly Leu Thr Pro Glu Lys Lys Ile Gly Ile Cys
65                  70                  75                  80

Ser Glu Asn Cys Leu Glu Phe Phe Ile Pro Val Leu Ser Gly Ala Tyr
                85                  90                  95

Ile Ala Ser Pro Val Ala Pro Thr Asn Glu Ile Tyr Thr Ile Arg Glu
            100                 105                 110

Leu Val His Ser Phe Gly Ile Ser Glu Pro Met Ile Val Phe Ser Ser
        115                 120                 125

Lys Lys Gly Leu Asp Lys Val Leu Glu Val Gln Lys Thr Val His Ser
    130                 135                 140

Ile Lys Thr Ile Val Ile Ile Asp Ser Ser Thr Thr Tyr Arg Gly Tyr
145                 150                 155                 160

Asp Ser Met Asp Ala Phe Val Lys Lys Tyr Val Pro Ala Asn Phe Asn
                165                 170                 175

Leu Ser Glu Phe Lys Thr Val Glu Val Asp Asn Glu Thr His Thr Leu
            180                 185                 190

Leu Ile Met Asn Ser Ser Gly Ser Thr Gly Leu Pro Lys Gly Val Leu
        195                 200                 205

Val Arg His Cys Gly Ala Val Thr Arg Phe Ser His Cys Arg Asp Pro
    210                 215                 220

Ile Phe Gly Asn Gln Val Ser Pro Gly Thr Ala Ile Leu Thr Val Val
225                 230                 235                 240

Pro Phe His His Gly Phe Gly Met Phe Thr Thr Leu Gly Tyr Phe Ala
                245                 250                 255

Cys Gly Tyr Arg Ile Val Met Leu Thr Lys Phe Asp Asp Glu Val Leu
            260                 265                 270

Leu Lys Thr Leu Gln Asp Tyr Lys Cys Thr Gly Val Ile Leu Val Pro
        275                 280                 285

Thr Leu Phe Ala Ile Leu Asn Arg Ser Glu Leu Leu Glu Lys Phe Asp
```

Leu Ser Asn Leu Thr Glu Ile Ala Ser Gly Gly Ala Pro Leu Ala Lys
305                 310                 315                 320

Glu Val Gly Glu Ala Val Ala Arg Arg Phe Asn Leu Pro Gly Val Arg
            325                 330                 335

Gln Gly Tyr Gly Leu Thr Glu Thr Thr Ser Ala Phe Ile Ile Thr Pro
            340                 345                 350

Glu Gly Asp Asp Lys Pro Gly Ala Ser Gly Lys Val Val Pro Leu Met
            355                 360                 365

Lys Val Lys Val Ile Asp Leu Asp Thr Lys Lys Thr Leu Gly Pro Asn
370                 375                 380

Arg Arg Gly Glu Ile Cys Val Lys Gly Pro Met Leu Met Thr Gly Tyr
385                 390                 395                 400

Glu Lys Asn Pro Thr Glu Thr Lys Glu Ile Ile Asp Glu Asp Gly Trp
            405                 410                 415

Leu His Ser Gly Asp Ile Gly Tyr Trp Asp Glu Asp His His Phe Phe
            420                 425                 430

Ile Val Asp Arg Leu Lys Ser Leu Ile Lys Tyr Lys Gly Tyr Gln Val
            435                 440                 445

Pro Pro Ala Glu Leu Glu Ser Val Leu Leu Gln His Pro Asn Ile Phe
450                 455                 460

Asp Ala Gly Val Ala Gly Ile Pro Asp Pro Glu Ala Gly Glu Leu Pro
465                 470                 475                 480

Gly Ala Val Val Leu Glu Lys Gly Lys His Leu Thr Glu Gln Glu
            485                 490                 495

Val Leu Asp Tyr Val Ala Gly Gln Val Tyr Asn Ala Lys Arg Leu Arg
            500                 505                 510

Gly Gly Val Arg Phe Val Asp Glu Val Pro Lys Gly Leu Thr Gly Lys
            515                 520                 525

Ile Asp Ala Lys Ala Ile Arg Glu Ile Leu Lys Lys Pro Gln Ala Lys
            530                 535                 540

Met
545

<210> SEQ ID NO 41
<211> LENGTH: 1638
<212> TYPE: DNA
<213> ORGANISM: Luciola kuroiwae

<400> SEQUENCE: 41
atggaaaaag aggaaaacgt catctacggc cccgagccct ctaccctgt ggaagaaggc     60 agcgccggca cccagctgca ccggttcatg gaaagatacg ccaagatggg cgccatctgc    120
ttcagcaatg ccctgaccgg ccaggacgtg acctacgccg agtacttcga cagaagcgtg    180
cggctggccg aggccctgag aaggcatgga ctgaccccg agaagaagat cggcatctgc    240
agcgagaact gcctggaatt tttcatcccc gtgctgagcg gcgcctatat cgcctctcct    300
gtggccccca ccaacgagat ctacaccatc cgcgagctgg tgcacagctt cggcatcagc    360
gagcccatga tcgtgttcag cagcaagaaa ggcctggaca ggtgctgga agtgcagaaa    420 accgtgcaca gcatcaagac catcgtgatc atcgacagca gcaccaccta ccggggctac    480
gacagcatgg acgccttcgt gaagaaatac gtgcccgcca acttcaacct gagcgagttc    540
aagaccgtgg aagtggacaa cgagacacac acctgctga tcatgaacag ctccggcagc    600
accggcctgc ctaaaggcgt gctcgtcaga cattgtggcg ccgtgacccg gttcagccac    660

```
tgcagagatc ccatcttcgg aaaccaggtg tcccccggca ccgccattct gaccgtggtg      720
cctttccacc acggcttcgg catgttcacc accctgggct acttcgcgtg cggctaccgg      780
atcgtgatgc tgaccaagtt cgacgacgag gtgctgctga aaaccctgca ggactacaag      840
tgcaccggcg tgatcctggt gcccaccctg ttcgccatcc tgaacagaag cgagctgctg      900
gaaaagttcg acctgagcaa tctgaccgag attgcctctg cggagccccc tctggccaaa      960
gaagtgggag aagccgtcgc cagacggttc aatctgcccg cgtgcggcca gggctacgga     1020
ctgactgaga caaccagcgc cttcatcatc acacccgagg cgacgataa gcctggcgcc      1080 tctggaaagg tggtgcccct gatgaaggtc aaagtgatcg acctggacac caagaaaacc     1140
ctgggcccca cagacggggc gagatctgt gtgaagggcc ccatgctgat gaccggctac      1200
gagaagaacc ccaccgagac aaaagagatc atcgacgagg acggctggct gcactctggc     1260
gacatcggct actgggacga ggaccaccac ttcttcatcg tggaccggct gaagtccctg     1320
atcaagtaca agggctacca ggtgccccct gccgagctgg aatctgtgct gctgcagcat     1380
cccaacatct tcgatgccgg cgtggccggc atccctgatc ctgaagctgg cgaactgcca     1440
ggcgctgtgg tggtgctgga aaaaggcaag cacctgacag agcaggaagt gctggactac     1500
gtcgccggcc aggtgtacaa cgccaagaga ctgagaggcg gcgtgcgctt cgtggatgaa     1560
gtgcctaagg gcctgaccgg caagatcgac gccaaggcca tcagagagat cctgaagaaa     1620
ccccaggcca agatgtga                                                   1638
```

<210> SEQ ID NO 42
<211> LENGTH: 545
<212> TYPE: PRT
<213> ORGANISM: Luciola kuroiwae

<400> SEQUENCE: 42

```
Met Glu Lys Glu Glu Asn Val Ile Tyr Gly Pro Glu Pro Phe Tyr Pro
1               5                   10                  15

Val Glu Glu Gly Ser Ala Gly Thr Gln Leu His Arg Phe Met Glu Arg
            20                  25                  30

Tyr Ala Lys Met Gly Ala Ile Cys Phe Ser Asn Ala Leu Thr Gly Gln
        35                  40                  45

Asp Val Thr Tyr Ala Glu Tyr Phe Asp Arg Ser Val Arg Leu Ala Glu
    50                  55                  60

Ala Leu Arg Arg His Gly Leu Thr Pro Glu Lys Lys Ile Gly Ile Cys
65                  70                  75                  80

Ser Glu Asn Cys Leu Glu Phe Phe Ile Pro Val Leu Ser Gly Ala Tyr
                85                  90                  95

Ile Ala Ser Pro Val Ala Pro Thr Asn Glu Ile Tyr Thr Ile His Glu
            100                 105                 110

Leu Val His Ser Phe Gly Ile Ser Glu Pro Met Ile Val Phe Ser Ser
        115                 120                 125

Lys Lys Gly Leu Asp Lys Val Leu Glu Val Gln Lys Thr Val His Ser
    130                 135                 140

Ile Lys Thr Ile Val Ile Ile Asp Ser Ser Thr Thr Tyr Arg Gly Tyr
145                 150                 155                 160

Asp Ser Met Asp Ala Phe Val Lys Lys Tyr Val Pro Ala Asn Phe Asn
                165                 170                 175

Leu Ser Glu Phe Lys Thr Val Glu Val Asp Asn Glu Thr His Thr Leu
            180                 185                 190
```

-continued

```
Leu Ile Met Asn Ser Ser Gly Ser Thr Gly Leu Pro Lys Gly Val Leu
            195                 200                 205

Val Arg His Cys Gly Ala Val Thr Arg Phe Ser His Cys Arg Asp Pro
210                 215                 220

Ile Phe Gly Asn Gln Val Ser Pro Gly Thr Ala Ile Leu Thr Val Val
225                 230                 235                 240

Pro Phe His His Gly Phe Gly Met Phe Thr Thr Leu Gly Tyr Phe Ala
                245                 250                 255

Cys Gly Tyr Arg Ile Val Met Leu Thr Lys Phe Asp Asp Glu Val Leu
            260                 265                 270

Leu Lys Thr Leu Gln Asp Tyr Lys Cys Thr Gly Val Ile Leu Val Pro
        275                 280                 285

Thr Leu Phe Ala Ile Leu Asn Arg Ser Glu Leu Leu Glu Lys Phe Asp
290                 295                 300

Leu Ser Asn Leu Thr Glu Ile Ala Ser Gly Gly Ala Pro Leu Ala Lys
305                 310                 315                 320

Glu Val Gly Glu Ala Val Ala Arg Arg Phe Asn Leu Pro Gly Val Arg
                325                 330                 335

Gln Gly Tyr Gly Leu Thr Glu Thr Thr Ser Ala Phe Ile Ile Thr Pro
            340                 345                 350

Glu Gly Asp Asp Lys Pro Gly Ala Ser Gly Lys Val Val Pro Leu Met
        355                 360                 365

Lys Val Lys Val Ile Asp Leu Asp Thr Lys Lys Thr Leu Gly Pro Asn
370                 375                 380

Arg Arg Gly Glu Ile Cys Val Lys Gly Pro Met Leu Met Thr Gly Tyr
385                 390                 395                 400

Glu Lys Asn Pro Thr Glu Thr Lys Glu Ile Ile Asp Glu Asp Gly Trp
                405                 410                 415

Leu His Ser Gly Asp Ile Gly Tyr Trp Asp Glu Asp His His Phe Phe
            420                 425                 430

Ile Val Asp Arg Leu Lys Ser Leu Ile Lys Tyr Lys Gly Tyr Gln Val
        435                 440                 445

Pro Pro Ala Glu Leu Glu Ser Val Leu Leu Gln His Pro Asn Ile Phe
450                 455                 460

Asp Ala Gly Val Ala Gly Ile Pro Asp Pro Glu Ala Gly Glu Leu Pro
465                 470                 475                 480

Gly Ala Val Val Leu Glu Lys Gly Lys His Leu Thr Glu Gln Glu
                485                 490                 495

Val Leu Asp Tyr Val Ala Gly Gln Val Tyr Asn Ala Lys Arg Leu Arg
            500                 505                 510

Gly Gly Val Arg Phe Val Asp Glu Val Pro Lys Gly Leu Thr Gly Lys
        515                 520                 525

Ile Asp Ala Lys Ala Ile Arg Glu Ile Leu Lys Lys Pro Gln Ala Lys
530                 535                 540

Met
545
```

<210> SEQ ID NO 43
<211> LENGTH: 1638
<212> TYPE: DNA
<213> ORGANISM: Luciola kuroiwae

<400> SEQUENCE: 43
atggaaaaag aggaaaacgt catctacggc cccgagccct tctaccctgt ggaagaaggc    60

```
agcgccggca cccagctgca ccggttcatg gaaagatacg ccaagatggg cgccatctgc      120
ttcagcaatg ccctgaccgg ccaggacgtg acctacgccg agtacttcga cagaagcgtg      180
cggctggccg aggccctgag aaggcatgga ctgacccccg agaagaagat cggcatctgc      240
agcgagaact gcctggaatt tttcatcccc gtgctgagcg cgcctatat cgcctctcct       300 gtggccccca ccaacgagat ctacaccatc cacgagctgg tgcacagctt cggcatcagc      360
gagcccatga tcgtgttcag cagcaagaaa ggcctggaca aggtgctgga agtgcagaaa      420
accgtgcaca gcatcaagac catcgtgatc atcgacagca gcaccaccta ccggggctac      480
gacagcatgg acgccttcgt gaagaaatac gtgcccgcca acttcaacct gagcgagttc      540
aagaccgtgg aagtggacaa cgagacacac accctgctga tcatgaacag ctccggcagc      600
accggcctgc ctaaaggcgt gctcgtcaga cattgtggcg ccgtgacccg gttcagccac      660
tgcagagatc ccatcttcgg aaaccaggtg tcccccggca ccgccattct gaccgtggtg      720
cctttccacc acggcttcgg catgttcacc accctgggct acttcgcgtg cggctaccgg      780
atcgtgatgc tgaccaagtt cgacgacgag gtgctgctga aaccctgca ggactacaag       840 tgcaccggcg tgatcctggt gcccacccctg ttcgccatcc tgaacagaag cgagctgctg     900
gaaaagttcg acctgagcaa tctgaccgag attgcctctg gcggagcccc tctggccaaa      960
gaagtgggag aagccgtcgc cagacggttc aatctgcccg gcgtgcggca gggctacgga     1020
ctgactgaga caaccagcgc cttcatcatc acacccgagg gcgacgataa gcctggcgcc     1080
tctggaaagg tggtgccccct gatgaaggtc aaagtgatcg acctggacac caagaaaacc    1140
ctgggcccca cagacggggg cgagatctgt gtgaagggcc ccatgctgat gaccggctac     1200
gagaagaacc ccaccgagac aaaagagatc atcgacgagg acggctggct gcactctggc     1260
gacatcggct actgggacga ggaccaccac ttcttcatcg tggaccggct gaagtccctg     1320
atcaagtaca agggctacca ggtgcccccct gccgagctgg aatctgtgct gctgcagcat    1380
cccaacatct tcgatgccgg cgtggccggc atccctgatc ctgaagctgg cgaactgcca     1440
ggcgctgtgg tggtgctgga aaaaggcaag cacctgacag agcaggaagt gctggactac     1500
gtcgccggcc aggtgtacaa cgccaagaga ctgagaggcg cgtgcgctt cgtggatgaa      1560 gtgcctaagg gcctgaccgg caagatcgac gccaaggcca tcagagagat cctgaagaaa     1620
ccccaggcca agatgtga                                                    1638
```

<210> SEQ ID NO 44
<211> LENGTH: 1923
<212> TYPE: DNA
<213> ORGANISM: Luciola kuroiwae

<400> SEQUENCE: 44

```
gttcggtata ctcgcgagtt cgggcaaaaa ataacaagta gcgcaagatg gaaaagaag       60 aaaatgtgat atacggtccc gagccgtttt accccgtcga gagggatct gcaggaacgc      120 aactgcacag atttatggag cgatacgcca aaatgggggc tatatgtttt tctaacgccc     180
tcacgggcca agatgtaacg tatgccgaat attttgaccg atcggttcgt ttagcggaag     240
ctttgagaag gcacggctta acgccagaga aaaaatcgg tatttgcagc gaaaattgct      300
tagaattttt cattccggtg ctttcgggag cgtatatcgc ttcacccgtc gctccaacta     360
acgaaattta cactatacgc gaattggttc acagttttgg aatatccgag ccaatgatcg     420
tgtttagctc aaagaaagga ttggataaag tcttggaagt acaaaaaaca gtgcactcta     480
ttaaaacaat agtcattatt gatagctcaa ctacttatcg aggatatgac agcatggatg     540
```

```
cgtttgttaa aaaatacgta cccgcaaatt tcaatttatc cgaattcaaa actgtagaag        600
tcgataatga aactcacact cttcttataa tgaactcgtc cggttccacc ggtctaccga        660
aaggtgtgct agtccgtcat tgtggggcag ttacaagatt ttctcattgc agggatccga        720 ttttttggtaa tcaagtttca ccaggcacag caatttttaac ggtcgttccg ttccatcatg      780
gctttggtat gttcactact ttaggatact ttgtttgtgg ataccgaatc gtaatgttaa        840
caaaatttga tgacgaagta ttgttgaaaa ccctacaaga ttataagtgt actagtgtta       900
tcctagtacc aactttgttc gctatcctta atagaagtga actactggag aaattcgact       960
tgtctaatct gactgaaatt gcatctggtg gtgccccatt agcaaagaa gttggggaag       1020 ccgttgccag aagatttaat cttcctggtg ttcgccaagg ttacggttta actgaaacca      1080
catccgcttt tattatcacc ccagaagggg atgacaaacc aggggcttct ggaaaagttg      1140
tgcctttaat gaaagttaaa gtgattgatc ttgacactaa gaaaacgctt ggtcctaacc       1200
gtcgtggaga aatttgcgtt aagggtccta tgttgatgac aggttacgag aagaatccta      1260
cagaaactaa agaaattatc gacgaagatg gttggctgca cagtggagat attgggtatt       1320
gggacgaaga tcatcacttc tttattgtag atcgtctcaa atccttaatc aaatacaaag       1380
gatatcaagt accacctgct gaattggaat ccgtactttt acaacatcca aatatatttg       1440
atgccggtgt tgccggaatt cccgatcccg aagccgggga gcttccgggt gctgtggttg      1500
tattagagaa aggaaaacat ctaactgaac aagaagtatt ggattacgtt gccggacaag      1560
tttacaacgc aaaacgttta cgcggtggcg ttcgttttgt agacgaggta cctaaaggtc       1620
tcactggaaa aattgacgca aaggcaatta gagaaattct taagaagccg caagctaaga      1680
tgtgaattga tttggagatt tttatttcaa cgtactattt taatatgacc accatcaaat       1740
tacacaacta ataactactt taggctactg ttatgtctcg acttctatt tatcatgcac       1800 ggctaattta gtattgcttt aaagggcaaa tttatgaaac tgttatgcct gttttatgct       1860
gtcccaagat ggtatatata ataaattcca aatgcaaaaa aaaaaaaaa aaaaaaaaa      1920 aaa                                                                      1923
```

<210> SEQ ID NO 45
<211> LENGTH: 32
<212> TYPE: DNA
<213> ORGANISM: Artificial
<220> FEATURE:
<223> OTHER INFORMATION: JP_Kuroiwa_C540T

<400> SEQUENCE: 45
tcaatttatc cgaatttaaa actgtagaag tc                                      32

<210> SEQ ID NO 46
<211> LENGTH: 30
<212> TYPE: DNA
<213> ORGANISM: Artificial
<220> FEATURE:
<223> OTHER INFORMATION: JP_Kuroiwa_G666A

<400> SEQUENCE: 46
attttctcat tgcagagatc cgattttgg                                           30

<210> SEQ ID NO 47
<211> LENGTH: 26
<212> TYPE: DNA
<213> ORGANISM: Artificial
<220> FEATURE:

<223> OTHER INFORMATION: JP_Kuroiwa_A1410T

<400> SEQUENCE: 47
cggtgttgcc ggtattcccg atcccg 26

<210> SEQ ID NO 48
<211> LENGTH: 543
<212> TYPE: PRT
<213> ORGANISM: Rhagophthalmus ohbai

<400> SEQUENCE: 48

```
Met Ala Asn Glu Ile Ile Leu His Gly Ala Lys Pro Arg Asp Pro Leu
1               5                   10                  15

Asp Leu Gly Thr Ala Gly Ile Gln Leu Tyr Arg Ala Leu Thr Asn Phe
            20                  25                  30

Ser Phe Leu Arg Glu Ala Leu Ile Asp Ala His Thr Glu Glu Val Val
        35                  40                  45

Ser Tyr Ala Asp Ile Leu Glu Asn Ser Cys Arg Leu Ala Lys Cys Tyr
    50                  55                  60

Glu Asn Tyr Gly Leu Arg Gln Asn Ser Val Ile Ser Val Cys Ser Glu
65                  70                  75                  80

Asn Ser Thr Ile Phe Phe Tyr Pro Val Ile Ala Ala Leu Tyr Met Gly
                85                  90                  95

Val Ile Thr Ala Thr Val Asn Asp Ser Tyr Thr Glu Arg Glu Leu Leu
            100                 105                 110

Glu Thr Leu Asn Ile Ser Lys Pro Glu Leu Val Phe Cys Ser Lys Lys
        115                 120                 125

Ala Ile Lys Asn Met Met Ala Leu Lys Arg Asn Val Asn Phe Ile Lys
    130                 135                 140

Lys Val Val Leu Leu Asp Ser Lys Glu Asp Met Gly Glu Ala Gln Cys
145                 150                 155                 160

Leu Ser Asn Phe Met Ala Arg Tyr Ser Glu Pro Asn Leu Asp Val Arg
                165                 170                 175

Asn Phe Lys Pro Arg Asp Phe Asp Ala Lys Glu Gln Val Ala Leu Ile
            180                 185                 190

Met Ser Ser Ser Gly Thr Thr Gly Leu Pro Lys Gly Val Val Leu Thr
        195                 200                 205

His Arg Asn Leu Ser Val Arg Phe Val His Cys Lys Asp Pro Leu Phe
    210                 215                 220

Gly Asn Arg Thr Ile Pro Ser Thr Ser Ile Leu Ser Ile Val Pro Phe
225                 230                 235                 240

His His Ala Phe Gly Met Phe Thr Thr Leu Ser Tyr Phe Ile Val Gly
                245                 250                 255

Leu Arg Val Val Leu Leu Lys Arg Phe Glu Glu Lys Phe Phe Leu Ser
            260                 265                 270

Thr Ile Glu Lys Tyr Arg Ile Pro Thr Ile Val Leu Ala Pro Pro Val
        275                 280                 285

Met Val Phe Leu Ala Lys Ser Pro Leu Val Asp Gln Tyr Asp Leu Ser
    290                 295                 300

Ser Ile Arg Glu Val Ala Thr Gly Gly Ala Pro Val Gly Thr Glu Val
305                 310                 315                 320

Ala Val Ala Val Ala Lys Arg Leu Lys Ile Gly Gly Ile Leu Gln Gly
                325                 330                 335

Tyr Gly Leu Thr Glu Thr Cys Cys Ala Val Leu Ile Thr Pro His Asp
            340                 345                 350
```

Asp Val Lys Thr Gly Ser Thr Gly Arg Val Ala Pro Tyr Val Gln Ala
    355                 360                 365

Lys Ile Val Asp Leu Thr Thr Gly Lys Ser Leu Gly Pro Asn Lys Arg
370                 375                 380

Gly Glu Leu Cys Phe Lys Ser Glu Ile Ile Met Lys Gly Tyr Phe Asn
385                 390                 395                 400

Asn Lys Gln Ala Thr Glu Glu Ala Ile Asp Lys Glu Gly Trp Leu His
                405                 410                 415

Ser Gly Asp Val Gly Tyr Tyr Asp Asp Gly His Phe Phe Val Val
                420                 425                 430

Asp Arg Leu Lys Glu Leu Ile Lys Tyr Lys Gly Tyr Gln Val Ala Pro
            435                 440                 445

Ala Glu Leu Glu Trp Leu Leu Leu Gln His Pro Ser Ile Lys Asp Ala
        450                 455                 460

Gly Val Thr Gly Val Pro Asp Glu Ala Ala Gly Glu Leu Pro Gly Ala
465                 470                 475                 480

Cys Ile Val Leu Gln Glu Gly Lys Ser Leu Thr Gln Glu Ile Ile
                485                 490                 495

Asp Tyr Ile Ala Glu Arg Val Ser Pro Thr Arg Ile Arg Gly Gly
            500                 505                 510

Val Val Phe Val Asp Asp Ile Pro Lys Gly Ala Thr Gly Lys Leu Val
        515                 520                 525

Arg Ser Glu Leu Arg Lys Leu Leu Ala Gln Lys Lys Ser Lys Leu
    530                 535                 540

<210> SEQ ID NO 49
<211> LENGTH: 1632
<212> TYPE: DNA
<213> ORGANISM: Rhagophthalmus ohbai

<400> SEQUENCE: 49
atggctaacg agatcatcct gcacggcgcc aagcccaggg acccctgga cctgggcacc    60 gccggcattc agctctacag ggccctgacc aacttctcct tcctgaggga ggccctgatc   120
gacgcccaca ccgaggaggt ggtgtcttac gccgacatcc tggagaacag ctgtagactg   180
gctaagtgct acgagaacta cggcctgcgc cagaacagcg tgatctccgt gtgcagcgag   240
aatagcacca tcttcttcta ccccgtgatc gccgccctgt acatgggcgt gatcaccgcc   300
accgtgaacg acagctacac cgagcgggag ctgctggaga ccctgaacat ctccaagccc   360
gaactggtgt tctgctccaa gaaggccatc aagaacatga tggccctgaa gaggaacgtg   420
aacttcatca agaaggtggt gctgctggac agcaaggagg atatgggcga ggcccagtgc   480
ctgagcaact tcatggcccg gtactccgag cccaacctgg acgtgagaaa cttcaagcca   540
agggacttcg acgccaagga gcaggtggcc cttattatgt cctcctctgg caccaccggc   600
ctgccaaagg gcgtggtgct gacccacagg aacctgagcg tgcgcttcgt ccactgcaag   660 gacccctgt tcggcaacag aaccatcccc tccacctcca tcctgtccat cgtgcccttc   720
caccacgcct tcggaatgtt cacaacccctg tcctacttca tcgtgggcct gagagtggtg   780
ctgctgaaga gattcgagga agttcttc ctgagcacca tcgagaagta cagaatccca   840
acaatcgtgc tggcccctcc tgtgatggtg ttcctggcta agagcccct ggtggaccag   900 tacgacctgt ccagcatcag agaggtggcc accggcggcg ccctgtggg caccgaggtt   960 gccgtggccg tggccaagcg gctgaagatc ggcggcatcc tccagggcta cggcctgacc  1020

```
gagacctgct gcgccgtgct gatcaccccc cacgacgacg tgaagaccgg ctccaccggc    1080
agggtagccc cctacgtgca ggctaagatc gtggacctga ccaccggcaa gtccctggga    1140
cctaacaaga gaggcgagct gtgcttcaag agcgagatca tcatgaaggg ctacttcaac    1200
aacaagcagg ccaccgagga ggccatcgac aaggagggct ggctgcactc cggcgacgtg    1260
ggatactacg acgacgatgg acatttcttc gtggtggacc ggctgaaaga gctgatcaag    1320
tacaagggct accaggtggc ccccgccgag ctggagtggc tgctgctcca gcacccatcc    1380
atcaaggatg ccggcgtgac cggcgtgccc gacgaggccg ccggcgagct gcccggcgcc    1440
tgcatcgtgc tccaggaggg caagagcctg accgagcagg agatcatcga ctacatcgcc    1500
gagcgagtgt ctcccaccaa gcgcatccgg ggcggagtcg tcttcgtgga cgacatcccc    1560
aagggcgcca ccggcaagct ggtgagaagc gagctgcgga agctgctggc ccagaagaag    1620
tccaagctgt aa                                                        1632
```